(12) United States Patent
Andrieux et al.

(10) Patent No.: US 8,198,507 B2
(45) Date of Patent: Jun. 12, 2012

(54) TRANSGENIC OR RECOMBINANT NON-HUMAN MAMMALS AND THEIR USES IN SCREENING PSYCHOACTIVE MEDICINES

(75) Inventors: Annie Andrieux, Grenoble (FR); Didier Job, Grenoble (FR); Eric Denarier, Grenoble (FR); Christophe Bosc, Grenoble (FR); Muriel Vernet, Grenoble (FR)

(73) Assignees: Institut National de la Sante Et de la Recherche Medicale - INSERM (FR); Commissariat a l'Energie Atomique Et Aux Energies Alternatives (FR)

( * ) Notice: Subject to any disclaimer, the term of this patent is extended or adjusted under 35 U.S.C. 154(b) by 0 days.

(21) Appl. No.: 11/798,455

(22) Filed: May 14, 2007

(65) Prior Publication Data
US 2009/0064353 A1 Mar. 5, 2009

Related U.S. Application Data

(63) Continuation of application No. 10/432,241, filed on Nov. 17, 2003, now abandoned.

(30) Foreign Application Priority Data

Nov. 24, 2000 (FR) .................................. 00 15240

(51) Int. Cl.
*A01K 67/027* (2006.01)
*C12N 15/00* (2006.01)
*C07H 21/04* (2006.01)
(52) U.S. Cl. ......... 800/18; 800/25; 435/320.1; 536/24.1
(58) Field of Classification Search .................. 800/18, 800/25; 435/320.1; 536/24.1
See application file for complete search history.

(56) References Cited

OTHER PUBLICATIONS

Skolnick et al., 2000, Trends in Biotech, vol. 18, p. 34-39.*
Tomasinsig et al., 2005, Current Protein and Peptide Science, vol. 6, p. 23-34.*
Smallwood et al., 2002, Virology, vol. 304, p. 135-145.*
Chattopadhyay et al., 2004, Virus Research, vol. 99, p. 139-145.*
Skolnick et al. 2000, Trends in Biotech, vol. 18, p. 34-39.
Capecchi, Mario R., 1989, TIG, vol. 5, No. 3, p. 70-76.
Bosc et al., 1996, PNAS, vol. 93, p. 2125-2130.
XP-002178084; STOP Proteins are Responsible for the High Degree of Microtubule Stabilization Observed in Neuronal Cells by Guillard et al.; *The Journal of Cell Biology*, vol. 142, No. 1; pp. 167-179; c. Jul. 1998.
"Changes in mRNA Abundance of Microtubule-associated proteins in the rat brain following electroconvulsive shock," by Pei et al.; *Rapid Science Publishers, Neuro Report*; Vo. 9, No. 3; pp. 391-394; c. Feb. 1998.

XP-002178083; "Genomic Structure and chromosomal Mapping of the Mouse STOP Gene (*Mtap6*)," by Denarier et al.,; *Academic Press*; pp. 791-793 & 796; c. 1998.
XP-002178082; "Nonneuronal Isoforms of STOP Protein are Responsible for Microtubule Cold Stability in Mammalian Fibroblasts;" by Denarier et al.; *The National Academy of Sciences*; pp. 6055-6060; c. 1998.
XP-00124412; Perikaryal Aggregation of Stop Proteins Analyzed in a Transgenic Model,: by Goudet et al., c. Mar. 2000.
XP-002200548; "Behavioral Disorders and Impairment of Synaptic Plasticity in STOP Deficient Mice," by Andrieux et al.; *Society for Neuroscience Abstracts*, pp. 1-2; c. 2001.
Kappel et al., 1992, Current Opinion in Biotechnology, vol. 3, p. 548-553.
Wall, R. J., 1996, Theriogenology, vol. 45, pp. 45, 57-68.
Sigmund, C., Jun. 2000, Arterioscler. Thromb. Vasc. Biol., p. 1425-1429.
Mogil et al., 1999, Pain. vol. 80, pp. 67-82.
Mercier et al., 1997, "The modification of milk protein composition through transgenesis: progress and problems," In: Transgenic Animals: Generation and use, Ed. Houdebine LM, Harwood Academic Publishers, The Netherlands pp. 473-482.
Houdebine, L-M., 2002, Journal of Biotechnology, vol. 98, pp. 145-160.
Rudinger, 1976, Peptide Hormones, Parsons, University Park Press, Baltimore, pp. 1-7.
Kaye et al., 1990, Proc. Natl. Acad. Sci. USA, vol. 87, pp. 6922-6926.
Andrieux, A., et al., "Microtubule Stabilizer Ameliorates Synaptic . . . ", Biol Psychiatry, vol. 60, pp. 1224-1230, (2006), Society of Biological Psychiatry.
Begou, M., et al., "The Stop Null Mice Model for Schizophrenia . . . ", Neuroscience, vol. 157, pp. 29-39, (2008), Elsevier Ltd.
Bouvrais-Veret, C., et al., "Microtubule-associated STOP Protein Deletion . . . ", J. Neurochem., vol. 104, pp. 745-756, (2008), International Society for Neurochemistry.
Baratier, J., et al., "Phosphorylation of Microtubule-associated STOP Protein . . . ", Journal of Biological Chemistry, vol. 281, No. 28, pp. 19561-19569, (2006).
Begou, M., et al., "Post-Pubertal Emergence . . . ", Synapse, vol. 61, pp. 689-697, (2007), Wiley-Liss, Inc.
Brenner, E., et al., "Hypoglutamatergic activity in the STOP KO mouse: a potential model for chronic untreated schizophrenia", 21 pages total.
Merenlender-Wagner, Avia et al., NAP, A Microtubule Interacting Peptide Affects Cognitive Behavior in the Stop Heterozygous Mouse—A Microtubule-Deficient Model of Schizophrenia, obtained from Summer Neuropeptide Conference (SNP) Stady V Meeting (International Symposium on Signal Transduction in Health and Disease), Oct. 22-24, 2008, pp. 174-175, abstract only, 3 pages.
Yamada, Kazuyuki et al., Male mice lacking the gastrin-releasing peptide receptor (GRP-R) display elevated preference for conspecific odors and increased social investigatory behaviors, Brain Research, 2000, pp. 20-26, vol. 870.

* cited by examiner

*Primary Examiner* — Shin-Lin Chen
(74) *Attorney, Agent, or Firm* — Thompson Coburn LLP

(57) ABSTRACT

The invention concerns transgenic or recombinant non-human mammals, wherein the expression of the gene coding for a microtubule associated protein (MAP) is modified (STOP gene) (inactivation or overexpression) and their uses in screening medicines useful in schizophrenia and schizo-affective disorders, with anxious, paranoiac or depressive component.

9 Claims, 16 Drawing Sheets

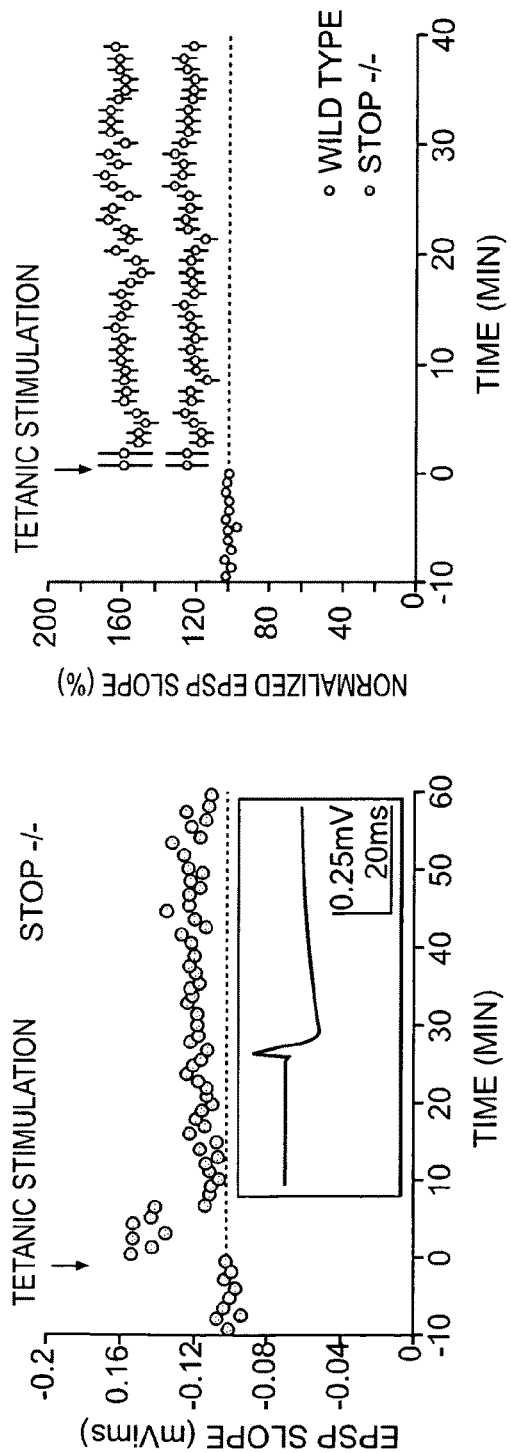

|  | % survival of newborns |
|---|---|
| wild-type primiparous females (n=6) | 93 % (45/48) |
| STOP -/- primiparous females (n=8) | 0 % (0/54) |
FIGURE 10a
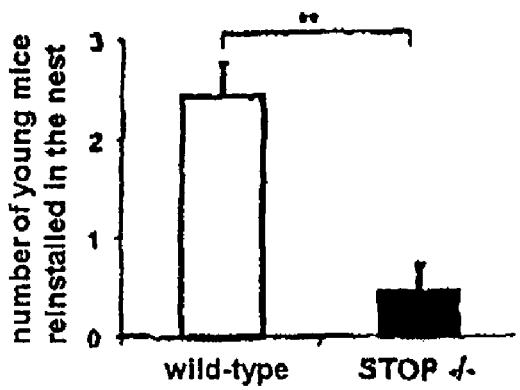
FIGURE 10b
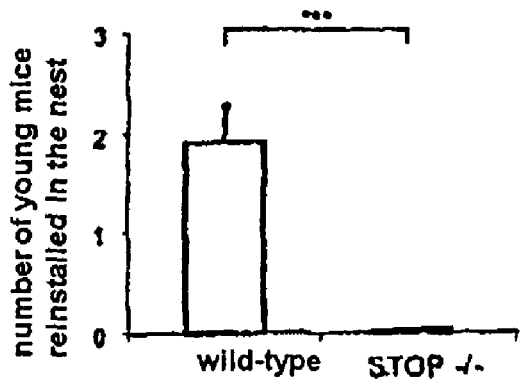
FIGURE 10c

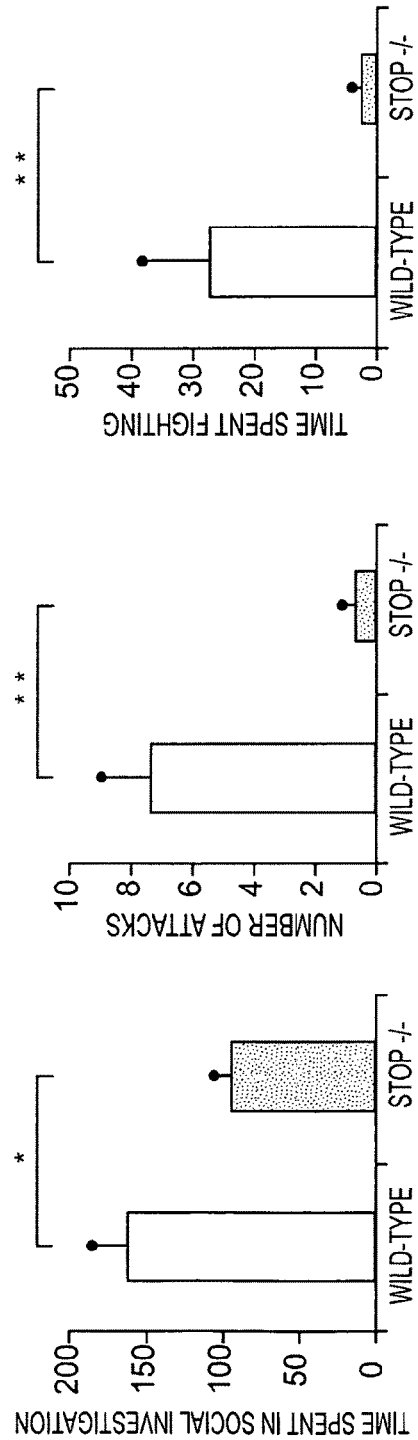

SEQUENCE LISTING

```
<160> NUMBER OF SEQ ID NOS: 6

<210> SEQ ID NO 1
<211> LENGTH: 7133
<212> TYPE: DNA
<213> ORGANISM: Mus musculus

<400> SEQUENCE: 1
gaattcaaag atgccattat cttgctttct ttcgtcccta cttctgatct cacggcagcc      60
ccagcagagg tcctatgagt cctccaagga ctacgtagct tcaacactga agcctgtaac     120
tttgtcccat ggtcccctaa tgcgtaagga aaaagcccag catttcacga taaagcagga     180
agcagagtga gtgcctttga tataataggg aaggtctaac ttacaggcta tttttaagaat   240 tgattgctaa gtatcaatat gatcacgctt ttaagatgac tcatgatctt ccacattaat    300
ctgttgtgtg tggaattata tctgtacatt gctggctatt aaaccatggc ttgctcctaa    360
cataaacact actaaatatc agattttct atctatctat ctatctattg atctatctat     420
ctatctatct atctatctac ctacctacct acctatcatc tatctatcta tcaatcatgt    480
atgtatgtat gtatgtatgt atgtatctat ctatctatct atctatctaa gtgtgtatga    540
gtgtagctgg gcataacatc acatgcttgt atgtagaggt aggaggacaa tcccttgaac    600
agatccctca tcaacaagtt ggatctggcc aaattggcat aagaaaaaaa aagctcaatg    660
tattatgttg ctaaagactt gcaaattaac aacaaatgta acccaaacag acacagcacc    720
aaacactggc aaggggggaga gaaacaggag ttctcattag ttactactga tcactcaaaa   780
ctggtacaac tatggtggaa gacagtttgt tttgttacaa aactaactca tcagttacta    840
ctgagtactc aaaactggta caattatggt ggaagacagt ttgctttgtt acaaaactag    900
ctattctttt ggccacataa tcacaatcct gctccttgat attacccaaa aagagcccaa    960
agcttatgtc agcacagaaa cctgaacact gttttagcag ctttgtttat aattccccc   1020 aattgaagca accagcatgc cattcagcag gtgacggata aataatctat gggaacacgt   1080
aatattcacg aacaagagaa atgagatacc agccatgaaa agatatgatg gatccttgag   1140
cttattacta agtcagagct aatctgaaac actgcttact atctgatgga tcaaaaagga   1200
ggaatctacc tcaggtgaca agatgaacct tgtcacctcc ttaagggtta atccagtgag   1260
acaggtgagg ggactgagag gatccacccc aggaaagaca tattcacctt acaataacgt   1320
actcttccct tacagaatta tggcctccta atgcagttcc cttgctatgc aagtgtgagc   1380
acatgagttc aagtcctgca cagtgaagca caaatcaggg tgtggtcagg tgagcacctg   1440
ggacctcagc actgtgaggg gcagagccag gaaaactgca ggggcttgct agccagtgag   1500
cctagcttca gattcagtga gaaaccttgt ttcatgggga aaaaggcaga gaatggtaga   1560
gcagaatacc cagcatcctc ccttagacgt acacatgtgc atatatgcca caaataaatt   1620
aattaagagt aaatatttgg gacttttaag aaaatgaact ctttcttttc cttgtgaagt   1680
agcagatttc caagtagcag gcttctcagt ggcttatctg ggaggctctg cctgtgagac   1740
ttttggataa gctttttgaat attaacaggt tctgctgaag aagccatttc tatatgccag   1800
```

```
gagctgcagc taatatttct tgtgaattgt gtcacttcag tcttcagaaa aactttgtaa    1860
gttcagaata gatacccttg ctcagagaca aagttaaggg tcagaggttg ccacaatttg    1920
tctatgcctt agagccaaaa gtgcagaagc caggatccaa atccctgagt atggactcca    1980
ggcttctgct ctgggtgctt aactttcctc atgaaaccac cccgaggcat ttattagctc    2040
tactaccctc ccccccccca cccccgccc cgacccaggg gactgcagcc cagagacaac      2100
ccaagtcaca aagagagtat cagagccaaa gcaggtccat tagattccaa aatctgttca    2160
accccaaagt agaaaagaag gcagaaacac aaccgagaat cccctcaaag aggtctccct    2220
tttcctaggg aactgtctct catccagccg cttacctcct cccttgggtc tctttccaga    2280
atcttccttt ttctcccttt cccccagtgc agcatctggg ctggagaaga accaattta     2340 tcctgggaga gtagactcac tgcttcccag ttgcttaaag aaggaacagc cagagtatgg    2400
ctaggccggc ttcccaggcc ggcctctccc aatctcatac aactggggaa gccctgtac     2460 acataggctt aggtcaagaa ccagcaacac ggagcataag tacagcctga tagctgacca    2520
attaactgca gctctccctt ttaaagtatc tattcagggg ctgagtggtt aaaaacttgt    2580
attggtgttc cagaggaccc aagtccgggt cccagcattc acatgggggt ggggtgggag    2640
ctcatagtcg cctgcacagc accagggaaa tctacttctg accctctggc ctcagcaggc    2700
accagagccc atgtgcatat acccaacaca gacaaaagca ctaattaaaa ggtggcgcaa    2760
ccctttaatc ccagcacttg ggaggcaaag gcaagcggct tttctgagtt caaggccagc    2820
ctggttacag actgagttcc aggacagcca agactacaga gagaaccct gttcgaaaaa     2880 acaaaagcca aaaccaaaa aaaaaaaaaa gtaaaaaaga ttttaaaag aagccaaagc      2940 atttagtctg aaacagacat ttcatggagg cggggcggtc ttacacttaa aaaattagta    3000
ttcattggtt ggggcgattt tacgaaagag aggagactcg gttttaggac atgaagctgg    3060
caactcaagg acagcaagtc ctcaggagct tgggacttga acctatcaag gacccagttc    3120
tgctgttgcc tgggaacaga aagggagga gctgccagag agaagggagg aggggacagg     3180
gagagggcaa cctttcagct gcgcgccctg acgacagcag gtgatttttt tttttttct     3240 gcagcgcgca tactctcagc atcttttctt gatcacccca cctcccttgc tgagccgcaa    3300
aaaagggtgg ggccgcctct ctgcagcaga agacgacagc ggcagcggct gcggcatcac    3360
cgggggtata gatagaggcc gttttgctct ctgctctgtc tgggttggag gtgaccgctg    3420
ccaagcctcg ctaggcggcc ggctgaacca gacagaaagg agataaaagc ctgcttgcga    3480
tccttcctgc gccatggctt aagcccacag cctctttgcc aagcatctcc ttgctctgcc    3540
ggggtctgct agacaccgca gtcgcagaga gggcgcgccc agacgcccta ggcctggact    3600
ctgggacgct gagcctcgct cctattcttc actgcccaca gcagctcctc tgcagcaggc    3660
gtttgcagcc ggcaatcgag ggactttacg gactttatct cagcggtacc ttgtccccgg    3720
gtgctctttg agggtggagg acgaggcaaa gggcttctaa gggaaggaag cggtgggaac    3780
cacattggcg ggtctgggtt ggggttaaag ggagattgga gatttgattt aggaccacaa    3840
aaaggctttg tggctaacat ggcgtggccg tgcatcacaa gggcctgctg catcgcccgc    3900
ttctggaacc agctggacaa ggcggacatt gcggtgccgc tggttttcac caagtactcg    3960
gaggccaccg aacacccagg cgcccctccg cagccgccag ctccgctgca gcccgcgtta    4020
gcgcccccct cgcgtgctgt cgccatagag acgcagccag cccagggaga gtcggatgca    4080
gttgcccggg caacagggct tgcgcccggg cccagcgtcg accgcgagac tgtagccgcc    4140
cccggccgga gcgggctggg cttgggcgcg gcctcagcct ccacttccgg ctcaggcccc    4200
```

```
gcggactcgg tgatgcgaca ggactaccgc gcctggaaag tgcagcggcc cgagccaagc   4260
tgccggccgc gcagcgagta ccagccgtcc gacgcgccct tcgagcgcga gacccagtac   4320
cagaaggact tccgcgcctg gccgctgccc cggcgcgggg accatccctg gatccccaag   4380
ccggtgcaaa tccctgcgac ttcgcagcct tcccaacctg ttctcggggt gcccaagcgt   4440
cggcctcaga gccaagagcg cgggcccatg caactttctg ctgatgcccg ggacccggag   4500
ggtgctggag gagccgggt gctggcggca ggaaaggcgt ccggtgtaga ccagcgcgac   4560
acacgtagga aggcagggcc agcatggatg gtgactcgca acgaagggca cgaagagaag   4620
cctctgcccc cagcccaatc ccagacccag gaggtggtc ctgcagctgg aaaggcgtcc   4680
ggtgcagatc agcgtgacac acgcaggaag gcagggccag catggatggt gactcgcagc   4740
gaagggcacg aagagaagcc tctgccccca gcccaatccc agaccaggga gggtggtcct   4800
gcagctggaa aggcgtccgg tgcagatcag cgtgacacac gcaggaaggc tggacccgcg   4860
tggatggtga ctcgcacgga agggcacgag gagacgccgc tgccacccgc ccagtctcag   4920
acccaggagg gcggccccgc agctggaaag gcatctggtg cagacgagcg cgacacgagg   4980
aggaaggcgg ggccggcctg gatggtgcgt cgctcggagg ggcacgaaca gacacccgct   5040
gcccatgccc aaggcacagg gcctgaagga agcaaggggc gcgcggtggc agatgccctc   5100
aacaggcaaa tccgggagga ggtggcgagt acagtaagca gctcttacag gtgagactgg   5160
ggcagcaggt gatgctggtc accctcatcc cctcgcgagg accacccatt ctaccccac   5220 accgaaagct tcgcattcag cttcttctcc agggccagac cacacctctt cagccacatt   5280
ccagaaccct ttcaacccag actttactgc ccaccctgtc ggaaagccct taacagtttc   5340
cacactggtt ttcccagctt gttttttgtg ccacccctaa gccacatttt cctcttggct   5400
gcctagctca gctccctatc tgccccacag agaccctgtc agtttccccc tgtctcatca   5460
gttcgcctgc tgtcccagcc tggctcccgt ccctagtcgc ctccactcat tcacttctca   5520
cttacttccc cgtgagaccc tttctcctcc ccagtctcac attgtcctgg tctcttccta   5580
ttgattcctc ccccagttct ggccgacact caagcgccac acccttttcc agatttctct   5640
acatgctcct taataactgg ctctagtact tgaagtcatt cccctcctgc ctcttcagta   5700
gctttgacac attgggcgag cttttttaacc ttcctgggcc ttcacattct tatctgtaac   5760
tgggatcaat aatagtcaac ttagaactat ccacacagga ctgatttaag ctgagatatt   5820
ctgtacagtt ttgaggatag actaaatgcc aaacatggct ctagctgatg gaaagtggaa   5880
agagatgact cgggatgact ggccatgcct gagatgtagt gagaggtctt gtttccattt   5940
atactctcct atgtgatgcc ccccttattct tgattctgct tcctggatgt ccctagccct   6000
cttccctgtt gaggcagctc ctttcttcct ttgtgttcag atgtttctat ttttctttt   6060 aattaattag ttaattaatt aatttactta ttcccttta atcctgctca ctgccccta   6120 cagtccttct ccccatgccc cacttcttct ctaagtgggt ggggtctccc cctgagtatc   6180
tccctaccct ggtacatcaa gtttctgcag ggctagtcta atcctctccc actcaggcca   6240
aacaagtcaa cccagctaga agaacatatt ccacgaacag ccaacagctt ttggggtag   6300 cccccattcc agttgtttgg gacccacatg aagaccaagc tgcacatctg ctgtatatgt   6360
gcagagaggt ctaggtccag cccatgtatg ctctttggtt tgtggttcag tctctgagaa   6420
cccctaaggg ttccaggtta gttgactctg ttgatcttcc tgtggagttc ctatctcctt   6480 agggggcctac aatccttctc cctatacttc cacaagactc cccaagctcc atccactgtt   6540
tggccatggg tgtctgtatc tgtctgagtc agctgctggg tggagcttct caaaggtcag   6600
```

```
acattaatgt gtcccttatc ctctggcaca ttcacgttcc ttgaaaatga acgctttcaa      6660
acttagaaac atccccatc ttcctccacg cacaccctgt ttatacaatt ctccctgtgc       6720
tgcatgcagc cttggcctgc tttctcacct cacatccatc cagtgcacat ctctgaatgt      6780
ttagcttttg ggccttcctt tatgtttcta ccaacatcag ctagctgata gatcctagtt      6840
gacttgaaca tgtagcagca ccgggcttgg gtactgagga agcagatgtg tgtgataatg      6900
atggagctgg ccttgtgcag ctgtgacttc tgaggtcttc attcagctcc acagtcagtt      6960
aggtgccctt ttcctaagtg tggaaggaag ggctacagag ttagtgtctt ctgctaaccc      7020
tgtgtgtggg cgcttcagta ggctctgcag gcactcctct catgcagcca gaagactggc      7080
ataaatagag actctattgt taaggcaaaa gtcagagccc tgcctcagaa ttc             7133

<210> SEQ ID NO 2
<211> LENGTH: 1881
<212> TYPE: DNA
<213> ORGANISM: Mus musculus

<400> SEQUENCE: 2
ctgtgagttg gtggccagct cggtttacat agtgagttcc aggacagcca gggcagaaaa       60
aaaaaaaaag tacctatata aaacttatga ggggctggtg agatggctca gtgggttaga      120
gcacccgact gctcttccga aggtccagag ttcaaatccc agcaaccaca tggtggctca      180
caaccatccg taatgagatc tgactccttc ttctggagtg tctgaagaca gctacaatgt      240
acttacatat aataaataaa taataaata aataaatctt aaaaaaaaaa acttatgaga      300
acatcggcgg agggacagtc ccttaaagag ccatttgtta tagctgaaga gatggtttca      360
ctggatagca gcacttgctg ctcttgcaga gaacccaggc tcagttcctc atccctatat      420
gatggttcgc aaccatttgt aactccagtt ccaggggaac caacgatacg tgtacataca      480
agcaggcaaa acacccacac tcataaaatg aaatacacaa ctcttaactg ttttttgttca     540 cctgtctcca ccccccagtgt tggggtagca gacacatgca gctatgccta acttttacgt     600
aagttctggg ggcctgaatt ccaatcttca tcccgatcca gcaagcactt ttacccctgt      660
agccatctcc ttggccttga gaaagcttct taagggttga tatcattccg aggaaaatat      720
tgaatacata tttactatgg agtcatgtat atttaagaaa tgcacacagc atgcatttat      780
gcctccttcc acgttctgga aacactggag gaaggtaggc agggagtgtg tttaggatgg      840
aatttaaaat ttatccgggc catttttattt aagggcatct cagatctatc accaaggatt     900
cccacttaga aaatttggac aacataagcc tcaaaatgaa aagtgaaaaa aatgggttaa      960
taccacagta aaatattca tgaatccgac agtgtataac aaagaggcca gctactaagt      1020
gtagaaagaa taaggattc tgagaaatca tcatgtgaca aacatcatca tagcgagtgt      1080
gctgggcaag ggacgccagc agttggtaaa tgatcgggcg acaattcctt gggtaacaaa      1140
caaacgagtt gcagagtgtc aggtgacctt gcttagtgta gtagttggac tggataatga      1200
atagcagagc accttgaaat ctgaggacgt tatagttgtt ttaaaaatgt cttcacaagg      1260
ccctcatgtt gtgtaaagga gattttaaaa ttttagttca acaaaagaa gacatgttta      1320 ctgtgtatct tagcctgttt tagttctggg acagacacca tagataccga gctgaaacaa      1380
caagtgctct ttacccacag ttccagggcg tgggaagtac aacatcaaag ctctgatgca      1440
agtggtgtcc gtgaggatcc atttcctgct atgcagatgc tgcaaacata tgactccggc      1500
ctcttcctct tctttaaggg catgtgtctg aagtgggggtg gggtggcatc ctcatgactt     1560
catctgtgtt ttccctagag atagccccttt tggttagggt tttaacatag atgtttggtg     1620
```

```
cacacataca tttagtctat gatagtctct agcaacagcc agttgggagg gaaggagagg    1680
gagagggaga gagagagaga gagagaacac atgtatgcga gtctgtgatt tctagcttct    1740
tagcttctta tatttgatct aattttcatt tattttatga ttctggaact ctgttgtttt    1800
attactttga aattctagga ctccaaataa atattttga tcttaaaata ttatcattat     1860
tttattctga tcccagaatt c                                              1881

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agagtcggat gcagttgccc ggcaaca                                        27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggctcctcca gcaccctccg ggtcccg                                        27

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aacagggtgt gcgtggagga a                                              21

<210> SEQ ID NO 6
<211> LENGTH: 1183
<212> TYPE: DNA
<213> ORGANISM: Mus musculus

<400> SEQUENCE: 6
gatatcattc cgaggaaaat attgaataca tatttactat ggagtcatgt atatttaaga    60
aatgcacaca gcatgcattt atgcctcctt ccacgttctg gaaacactgg aggaaggtag    120
gcagggagtg tgtttaggat ggaatttaaa atttatccgg gccattttat ttaagggcat    180
ctcagatcta tcaccaagga ttcccactta gaaaatttgg acaacataag cctcaaaatg    240
aaaagtgaaa aaaatgggtt aataccacag taaaaatatt catgaatccg acagtgtata    300
acaaagaggc cagctactaa gtgtagaaag aataaaggat tctgagaaat catcatgtga    360
caaacatcat catagcgagt gtgctgggca agggacgcca gcagttggta aatgatcggg    420
cgacaattcc ttgggtaaca aacaaacgag ttgcagagtg tcaggtgacc ttgcttagtg    480
tagtagttgg actggataat gaatagcaga gcacctgaa atctgaggac gttatagttg     540
ttttaaaaat gtcttcacaa ggccctcatg ttgtgtaaag gagattttaa aattttagtt    600
caacaaaaag aagacatgtt tactgtgtat cttagcctgt tttagttctg ggacagacac    660
catagatacc gagctgaaac aacaagtgct ctttacccac agttccaggg cgtgggaagt    720
```

```
acaacatcaa agctctgatg caagtggtgt ccgtgaggat ccatttcctg ctatgcagat        780
gctgcaaaca tatgactccg gcctcttcct cttctttaag ggcatgtgtc tgaagtgggg        840
tggggtggca tcctcatgac ttcatctgtg ttttccctag agatagcccc tttggttagg        900
gttttaacat agatgtttgg tgcacacata catttagtct atgatagtct ctagcaacag        960
ccagttggga gggaaggaga gggagaggga gagagagaga gagagagaac acatgtatgc       1020
gagtctgtga tttctagctt cttagcttct tatatttgat ctaattttca tttattttat       1080
gattctggaa ctctgttgtt ttattacttt gaaattctag gactccaaat aaatattttt       1140
gatcttaaaa tattatcatt attttattct gatcccagaa ttc                         1183
```

TRANSGENIC OR RECOMBINANT NON-HUMAN MAMMALS AND THEIR USES IN SCREENING PSYCHOACTIVE MEDICINES

CROSS REFERENCE TO RELATED CASES

This application is a continuation of U.S. patent application Ser. No. 10/432,241, filed Nov. 17, 2003 now abandoned, which is incorporated by reference herein in its entirety. The present invention relates to transgenic or recombinant non-human mammals in which the expression of the gene encoding a microtubule-associated protein (MAP) is modified (inactivation or overexpression) and to their uses in screening medicinal products of use in anxiety, schizophrenia and schizoaffective disorders with a component of anxiety, paranoia or depression.

The microtubules of mammalian cells are subjected to regulation: during interphase, they organize the intracellular space and are responsible for the intra-cellular transport of organelles; during mitosis, they reorganize to form the mitotic spindle responsible for distributing the chromosomes between the two daughter cells.

Microtubules, assembled in vitro using solutions of purified tubulin, are labile and rapidly depolymerized by exposure to cold.

Similar behavior is observed in vivo, but, in this case, it is regulated by the cellular metabolism. For example, microtubule depolymerization is promoted by the phosphoprotein stathmin, which binds and sequesters the tubulin dimers, whereas microtubule stabilization is mediated by microtubule-associated proteins (MAPs), which associate with the polymers.

Neurons contain massive amounts of microtubules and said microtubules are virtually completely stable in response to cold. A calmodulin-regulated protein 35 capable of completely stabilizing microtubules (i.e. able to suppress their dynamic activity and to make them resistant to cold) has been isolated from preparations of stable neuronal microtubules; this is
the STOP (for Stable Tubulin Only Polypeptide) protein. The molecular nature of this protein has remained enigmatic for a long time. A decisive step was taken in 1996 when the cDNA encoding this STOP protein was cloned (Christophe Bose et al., *PNAS.*, 1996, 93, 2125-2130).

The STOP protein, which can reversibly block the dynamics of microtubules by completely abolishing the sensitivity of neuronal microtubules to cold and to depolymerizing drugs, comprises two notable repeat domains: a central domain composed of five virtually complete repeats of a 46 amino acid motif, and a carboxy-terminal domain made up of twenty-eight incomplete repeats of an 11 amino acid motif. These two repeat domains are separated by a sequence containing an abundance of lysine and arginine residues (KR domain) and by a linker sequence. The N-terminal domain of the STOP protein contains proline-rich sequences which constitute potential sites for binding with SH3 domains (src homology domain 3).

The exon structure of the mouse STOP gene has been elucidated (Eric Denarier et al., BBRC., 1998, 243, 791-796). This structure corresponds to the domain structure of the protein: exon 1 encodes the N-terminal domain including the central repeat domain, exon 2 encodes the linker sequence, exon 3 encodes the KR domain and exon 4 encodes the carboxy-terminal repeat region.

The distribution and the role of the STOP protein in neurons have recently been characterized (Laurent Guillaud et al., *Cell Biol.,* 1998, 142, 1, 167-179). The distribution of the protein has been studied at the ultrastructural level in embryonic neuronal cells, DRG (Dorsal Root Ganglia) cells, which can differentiate in vitro, and has revealed the existence of isoforms of this protein. A major isoform (E-STOP protein) has been characterized: this isoform appears earlier in development than the standard STOP protein or N-STOP protein, and is the major form in the embryonic brain. The cDNA of E-STOP has the sequence corresponding to Genbank accession number AJ002556. The E-STOP protein differs from the N-STOP protein by the deletion of the carboxy-terminal repeat sequences, encoded by exon 4; it is therefore a splice variant of the STOP protein. Another isoform, the F-STOP protein has been observed in mice fibroblasts (3T3 cells). This protein, which has an apparent molecular mass of 45 kDa, is much smaller than the N-STOP protein (115 kDa) or the E-STOP protein (88 kDa). The cloning and the sequencing of the corresponding cDNA (Genbank Y16032 and Eric Denarier et al., PNAS., 1998, 95, 6055-6060) have shown that the sequences encoded by exons 3 and 4 (KR and carboxy-terminal repeats) are absent in the F-STOP protein. In addition, the major part of the N-terminal domain of the N-STOP protein, located upstream of the central repeats and encoded by exon 1, is absent in the F-STOP protein. The F-STOP protein therefore comprises the sequences encoded by exon 2 and a part of those corresponding to exon 1, including the central repeats. Despite multiple deletions, the F-STOP protein has the same basic functional properties as the N-STOP protein: the F-STOP protein binds to calmodulin and has the ability to induce microtubule stabilization with respect to cold, in vitro and in vivo. Unlike the N-STOP protein, which appears to be almost permanently associated with the microtubules, the F-STOP protein remains in the soluble phase in cells in interphase and only associates with the microtubules during exposure to cold. Apparently, regulatory mechanisms prevent the F-STOP protein interacting with the microtubular cytoskeleton in interphase, thus allowing rapid microtubular dynamics, and this regulation is inhibited as soon as the cells are exposed to low temperatures. In mitotic cells, the F-STOP protein is associated with the microtubule spindles, at physiological temperature. Thus, a single and same class of proteins, the STOP proteins, is responsible for microtubule stabilization in several different cellular types.

The N, E and F forms of the STOP protein are not the only isoforms which exist; specifically, the STOP proteins are present in many tissues, in particular in the lungs, which contain a specific isoform. Similarly, the F-STOP form appears to be present in varied tissues. On the other hand, the N-STOP and E-STOP proteins are, it appears, strictly neuronal (C. Bose et al., *Cell Struct. Function,* 1999, 24, 393-399).

It would seem that microtubule stability is important for the development and maintenance of the morphology and function of neurons (Laurent Guillaud et al., mentioned above). Thus, it has been shown that inhibition of the STOP proteins in vitro by injecting specific blocking antibodies suppresses microtubule stability with respect to cold in neuronal or non-neuronal cells (Eric Denarier, PNAS, 1998, mentioned above). It has also been shown that inhibition of the STOP proteins in vitro in neurons impairs neuronal differentiation (Laurent Guillaud et al., mentioned above).

The inventors have found, unexpectedly, that knocking out the various isoforms of the STOP protein makes it possible to obtain animals, and in particular mice, which are of particular use for screening psychoactive medicinal products.

Consequently, a subject of the present invention is a recombinant non-human mammal carrying at least one modified allele of the gene encoding a STOP protein.

The term "modified STOP gene" is intended to mean both an altered gene (knock-in animals) and an inhibited or truncated totally or partially inactivated gene (knock-out animals).

Advantageously, said recombinant or transgenic animals can be obtained by homologous recombination in an embryonic stem cell:
either by insertion of at least one STOP codon or of an antisense sequence,
or by deletion of part or all of the native gene (coding region or noncoding regions, promoter, 3' regulatory sequences, activators),
or by sequence substitution.

More precisely, a construct in accordance with the invention is advantageously selected from the group consisting of:
constructs containing a sequence encoding a STOP protein which is antisense, which will block expression of the native STOP sequence,
constructs comprising the region of the STOP promoter (positions 1-3400 of FIG. 2) in combination with a reporter gene or with the STOP coding region. Markers for positive or negative selection can advantageously be included, such as lacZ, the regulation and expression of which will lead to the detection of a change in the phenotype. A preferred reporter gene is the GFP (green fluorescent protein) gene,
constructs comprising at least one portion of the STOP gene (coding region or noncoding regions, promoter, 3' regulatory sequences, activators) including the desired modification(s) (deletions, mutations, etc.); advantageously, the DNA constructs used for a targeted integration should include a region exhibiting homology with the target sequence (STOP gene), so as to induce a recombination,
constructs comprising at least one portion of the STOP gene, functionally linked to a promoter, which may be constitutive or inducible, and to other regulatory sequences required for expression in the host animal. The term "functionally linked" is intended to mean that a DNA sequence and a regulatory sequence are combined in such a way that they allow expression of the gene when the appropriate molecules, for example the transcription-activating proteins, are bound to the regulatory sequences.

For the purpose of the present invention, the term "STOP gene" is intended to mean the STOP genes obtained from any mammal, such as rat, mouse, bovine or human, or from chicken or from blowfish, and also the various mutated forms of said STOP gene; it also includes the various open reading frames, the exons, the introns, the 3' and 5' noncoding regions involved in regulating the expression of this gene, up to approximately 4 kb on either side of the coding region, the promoter and the activators.

Preferably, the constructs are selected from the following constructs:
constructs which include a fragment of the genomic sequence encoding a STOP protein, included between the initiation codon and the STOP codon (C. Bose et al., E. Denarier et al., L. Guillaud et al., mentioned above), including in particular all the introns normally present in the native chromosome. It may include the 3' and 5' untranslated regions found in the mature mRNA. It may also include transcription or translation regulatory sequences (promoter, activator, etc.), including approximately 4 kb, of the 3' or 5' flanking genomic regions;
constructs which do not comprise the region between positions 4118 and 5131 of the genomic sequence encoding a STOP protein;
constructs comprising 4.1 kb of the STOP gene (corresponding to positions 1-4118 of FIG. 2), the gene encoding β-galactosidase, placed under the control of the endogenous STOP promoter, a neomycin resistance gene under the control of the PGK promoter, 1.57 kb of sequence of the STOP gene (corresponding to positions 5131-6701 of the sequence of FIG. 2) and, finally, the thymidine kinase gene under the control of the PGK promoter.

In accordance with the invention, the transgenic animals obtained constitute two groups, the knock-out animals and the knock-in animals.

In the context of the present invention:
the knock-out animals have a partial or complete loss of function in one or both alleles of the gene encoding an endogenous STOP protein; such a modified gene no longer induces expression of the corresponding STOP protein. The knock-out animals according to the invention also include conditional knock-out animals: (i) modification of the gene encoding a STOP protein, which only becomes involved after exposure of the animal to a substance which induces the modification of said gene, (ii) introduction of an enzyme which induces recombination at a site of the gene encoding a STOP protein (Cre in the Cre-lox system, for example) or (iii) another method which induces a modification of the gene encoding a STOP protein after birth;
the knock-in animals exhibit a transgene which alters the endogenous gene encoding a STOP protein. A knock-in animal corresponds to an alteration in the host's cells which leads to a modified expression or a modified function of the native STOP gene. An increased or decreased expression can thus be obtained by introduction of an additional copy of the STOP gene or by functional insertion of a regulatory sequence which produces a significantly increased expression of an endogenous copy of the STOP gene. These changes can be either constitutive or conditional, as a function of the presence of an activator or of a repressor. The exogenous gene is either obtained from a species which is different from that of the host animal, or is modified in its coding or noncoding sequence. The gene introduced may be a wild-type gene or a manipulated sequence, for example exhibiting deletions, substitutions or insertions in the coding or noncoding regions.

The two methods may be combined: first, the gene of origin is knocked-out, then, secondly, a modified form of said gene is introduced into said animal.

The recombinant or transgenic animals thus obtained comprise an exogenous nucleic acid sequence, either present in the form of an extrachromosomal element, or stably integrated into all or some of the cells of said animal, more particularly the germinal cells.

Surprisingly, the homozygous mice containing the two alleles of the inactivated STOP gene (knock-out or STOP KO (−/−) mouse), obtained by crossing heterozygous animals, are viable and exhibit no anatomical modification of the brain; on the other hand, they exhibit deficiencies in synaptic plasticity, associated with multiple major behavioral disorders comprising a complete lack of mothering, profound anxiety, an inability to recognize objects, and abnormal social interactions.

Advantageously, these multiple behavioral disorders can be improved by prolonged administration of neuroleptics.

Consequently, the mice in which the STOP gene has been inactivated (STOP KO (−/−) mice) constitute a particularly useful model for studying and treating diseases involving a synaptic defect which are sensitive to neuroleptics, in particular schizophrenia and schizoaffective disorders with a component of anxiety, paranoia or depression.

A subject of the present invention is also the use of said recombinant non-human mammal carrying at least one allele of the gene encoding a modified STOP protein, for selecting or screening psychoactive products.

A subject of the present invention is also nucleic acid molecules comprising the sequence of a modified allele of the gene encoding a STOP protein as defined above (in particular the sequences of inactivated STOP genes), excluding the sequences corresponding to GENBANK accession numbers AJ002556 and Y16032.

The STOP sequences according to the invention are in particular obtained by mutation, in various ways known in themselves, so as to generate the desired targeted modifications: substitutions, insertions or deletions in a domain or an exon, which lead to the expression of an inactivated STOP protein or to the absence of expression of STOP protein. The deletions may include considerable modifications: deletion of a domain or of an exon (exon 1 in particular).

The fragments of said sequences are advantageously obtained by chemical synthesis of oligonucleotides, by enzyme digestion or by PCR amplification for example.

Said fragments comprise at least 15 nucleotides, preferably approximately 18 nucleotides, and preferably at least 50 nucleotides.

Such fragments are of use as PCR primers or for screening by hybridization, of the recombinant ES clones or of the recombinant animals.

Said primers or probes for screening recombinant ES clones or recombinant animals are characterized in that they are selected from the group consisting of fragments of a STOP gene comprising at least 15 nucleotides, preferably approximately 18 nucleotides, and preferably at least 50 nucleotides. Such primers or probes make it possible to screen cells or animals comprising one of the modified sequences as defined above.

Preferably, the following primers are used for the screening:
  oligonucleotide A4080: positions 4067-4095 of FIG. 2 (SEQ ID No. 3);
  oligonucleotide 770: positions 4488-4515 of FIG. 2 (SEQ ID No. 4);
  oligonucleotide AS2: positions 6680-6701 of FIG. 2 (SEQ ID No. 5).

Larger fragments (more than 100 nucleotides) are of use for producing the STOP proteins.

Sequences homologous to the cloned STOP sequences are identified by various methods known to those skilled in the art.

The nucleic acid sequence similarity is detected by hybridization under low stringency conditions, for example at 50° C. and 10×SSC (0.9 M saline buffer and 0.09 M sodium citrate).

Said sequences remain associated when they are subjected to washing at 55° C. in a 1×SSC buffer.

The identity of the sequences can be determined by hybridization under stringent conditions, for example at 50° C. at most and 0.1×SSC (9 mM of saline buffer/0.9 mM of sodium citrate).

A subject of the present invention is also probes for detecting and for screening the genomic DNA by hybridization of the recombinant ES clones or of the recombinant animals, characterized in that they consist of a fragment of the same STOP gene, located outside (upstream or downstream) the sequence of the STOP gene derived from the recombination vector used (region of homologous recombination).

Advantageously, said probe corresponds to positions 700-1881 of FIG. 3 (SEQ ID No. 6).

A subject of the present invention is also a method for screening and selecting molecules of use in the treatment of schizophrenia and schizoaffective disorders with a component of anxiety, paranoia or depression, characterized in that it comprises at least the following steps:
  bringing at least one substance to be screened into contact, in vitro, with a biological sample consisting of an extract of cells or organ slices, preferably of neurons or brains, obtained from at least one recombinant non-human mammal carrying at least one modified allele of the gene encoding a STOP protein,
  measuring the action of said substance to be screened on said cells or organ slices, and
  comparing the values obtained with those of the cells or of the organ slices of a biological sample obtained from a non-human mammal of the same type, carrying two wild-type alleles of the gene encoding a STOP protein.

The substances tested are in particular obtained from libraries of substances (natural or synthetic).

According to an advantageous embodiment of said method, said measurement is carried out using a protein-protein binding assay; in such a case, one or more of the molecules used can be labeled with a label; said label can provide a signal which is detectable either directly or indirectly.

Among the labels which can be used, mention may, for example, be made of radioisotopes, fluorescent or chemiluminescent molecules, enzymes, specific binding molecules, particles such as magnetic particles, etc.

Specific binding molecules include pairs of molecules such as biotin and streptavidin, digoxin and anti-digoxin, etc.

For the specific binding members, the complementary member will be labeled with a molecule suitable for detection, in accordance with known methods.

Many other reagents can be used in such a screening assay; it includes, for example, salts, neutral proteins such as albumin, detergents, etc., which are used to facilitate optimal protein-protein binding and/or to reduce the nonspecific interactions or the background noise interactions.

Reagents which improve the effectiveness of the assay, such as protease inhibitors, nuclease inhibitors or antimicrobial agents, can also be used.

The mixture of components is added in any order, so as to allow the desired binding.

The incubations are carried out at a suitable temperature, usually between 4° C. and 40° C.

The incubation periods can vary; they are conventionally between 0.1 and 1 h and are optimized within this time range, in particular so as to facilitate rapid screening.

Antibodies specific for STOP protein polymorphisms can be used in screening immunoassays, more particularly to detect the binding of the substrate or of STOP protein or to confirm the absence or presence of a STOP protein in a cell or a sample, such as a biological sample.

According to another advantageous embodiment of said method, said measurement is carried out by detection of the variation in intensity of an electrical signal; specifically, it is possible to observe, as regards the nerve cells of the recombinant animals according to the invention, an alteration in the organization of the synapse (positioning and transport of neuroreceptors) in the recombinant animals according to the invention.

The present invention also relates to a method for screening and selecting molecules of use in the treatment of anxiety, schizophrenia and schizoaffective disorders with a component of anxiety, paranoia or depression, which method is characterized in that it comprises:

administering at least one substance to be screened to at least one recombinant non-human mammal carrying at least one modified allele of the gene encoding a STOP protein; and studying the behavior of said mammal compared to a series of control animals and/or determining the location of the medicinal products after their administration.

Such animals can advantageously be used as models for screening psychoactive molecules exhibiting low toxicity in humans.

A subject of the present invention is also a vector for homologous recombination of a gene encoding a STOP protein, characterized in that it comprises a nucleotide sequence of a modified STOR gene encoding an inactivated STOP protein, preferably truncated in at least one of the exons, in particular exon 1.

A subject of the present invention is also a method for producing recombinant non-human mammals carrying at least one allele of the gene encoding an inactivated STOP protein, characterized in that:

an allele of the gene encoding a STOP protein is truncated;

said modified sequence is introduced into a segment of the genomic DNA of a non-human mammal of the same type, associated with a suitable label, so as to obtain a labeled sequence M containing said modified allele;

said sequence M is integrated, in vitro, into the stem cells of germinal lines of embryos of a non-human mammal by transfection and the cells which have said allele through homologous recombination events are selected; then said selected stem cells are reinjected into an embryo which is reimplanted into a non-human mammal of the same type, in order to obtain chimeric animals; and in the F1 generation, recombined heterozygous non-human mammals are obtained and, in the F2 generation, recombined STOP −/− homozygous non-human mammals, recognizable by the presence of the label, and "wild-type" (+/+) mice are obtained.

A subject of the present invention is also the use of the substances selected using the screening method as defined above, for preparing a medicinal product of use in the treatment of schizophrenia and schizoaffective disorders with a component of anxiety, paranoia or depression.

Besides the preceding arrangements, the invention also comprises other arrangements, which will emerge from the following description, which refers to examples of implementation of the method which is the subject of the present invention, with reference to the attached drawings in which:

FIG. 1 illustrates the genomic organization of the STOP gene at exon 1 and the establishment of knock-out mice for the STOP gene [STOP KO (−/−) mice] by alteration of exon 1. A: restriction map of a fragment of the STOP gene (wild-type allele) used for producing a genomic homology fragment, structure of the homologous recombination vector or screening vector ptSTOP, and predicted structure of mutant allele. EV: EcoRV; EI: EcoRI; TK: thymidine kinase; pgk: phospho-glycerate kinase; neo: neomycin; NTR: Nucleotide Translation Region. B: Southern blotting profiles for the STOP gene in wild-type mice (+/+; 8 kb) and hetero-zygous mice (+/−; 5.3 kb);

Figure 2:
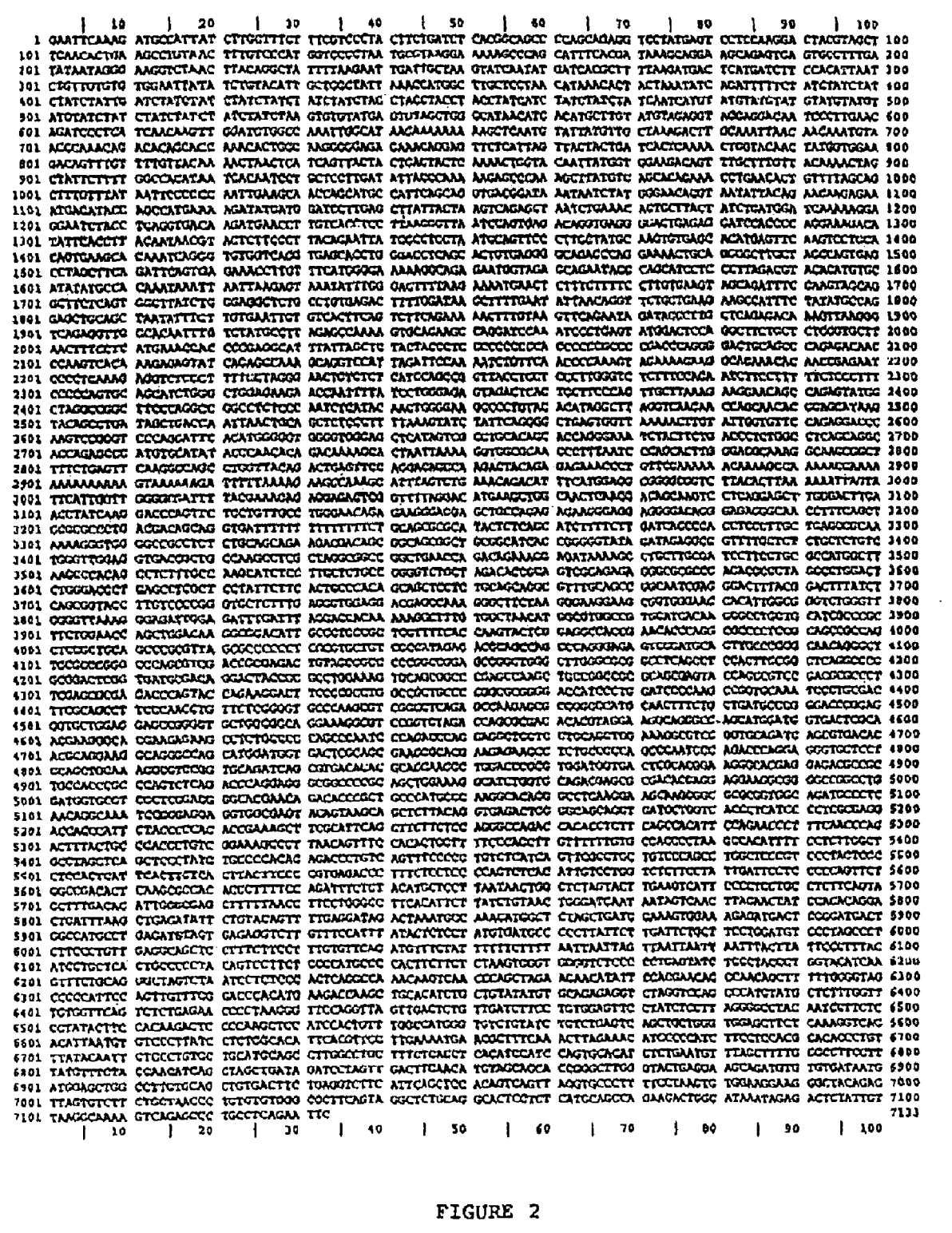

FIG. 2 represents the sequence (SEQ ID NO: 1) of the STOP gene at exon 1 (positions 3333-5150) (7.2 kb genomic clone); the fragments used to establish the STOP KO (−/−) mice are as follows: 5' homologous sequence: 4.118 kb, positions 1-4118; 3' homologous sequence: 1.57 kb, positions 5131 to 6701;

Figure 3:
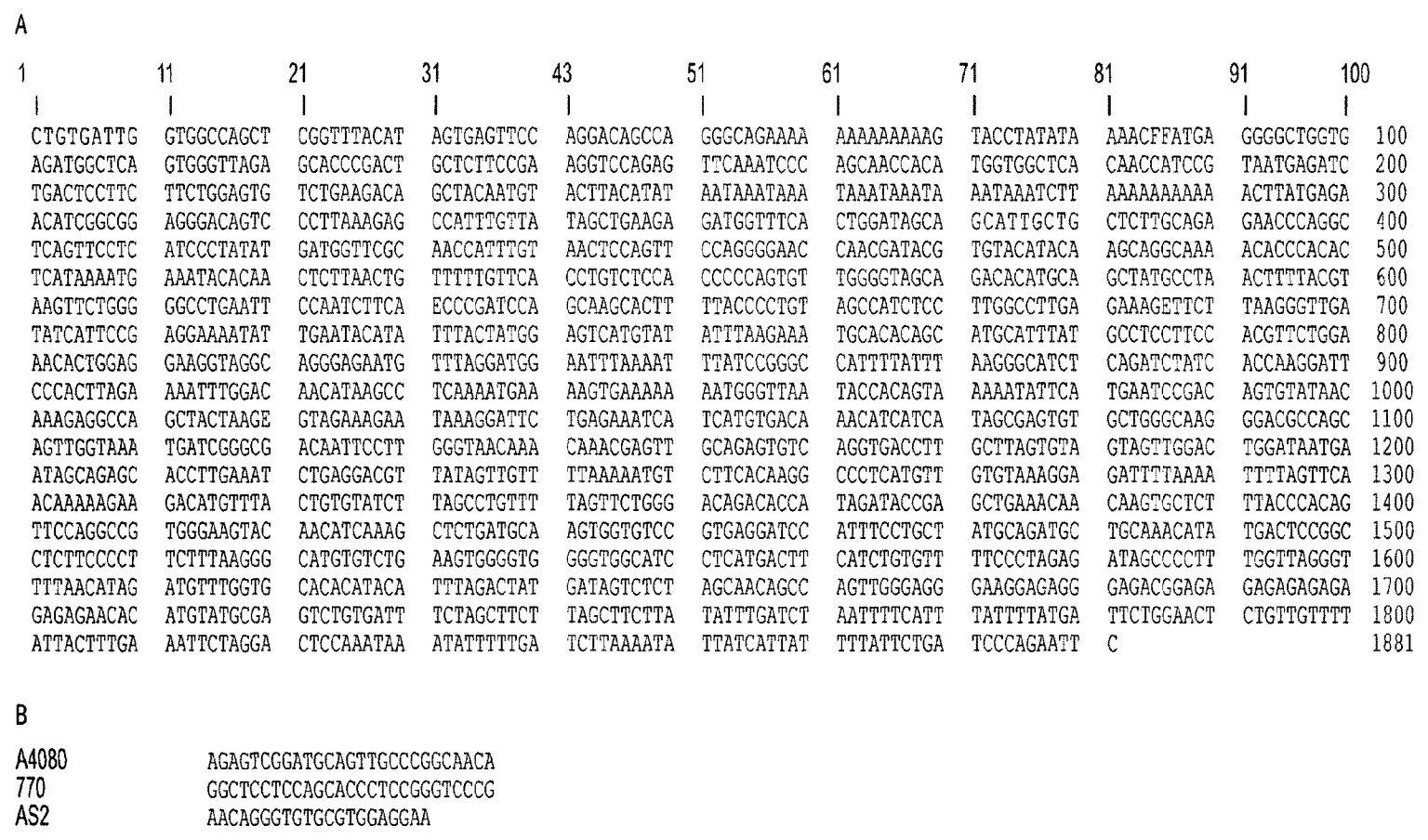

FIG. 3: FIG. 3A represents the genomic sequence (SEQ ID NO: 2 of the STOP gene, located in the 5' position relative to the sequence of FIG. 2, and FIG. 3B represents the probe (SEQ ID NOS 3-5, respectively, in order of appearance) used for the screening, which is an EcoR V-EcoR I fragment (positions 701-1881 on FIG. 3A);

FIG. 4 illustrates the Western blotting analysis, using the polyclonal antibody 23C (Laurent Guillaud et al., mentioned above), of the expression of the STOP (E-STOP and N-STOP) proteins in the brain of the STOP KO (−/−) or wild-type mice. This figure shows the absence of STOP proteins in the brain of the STOP KO (−/−) mice compared with the wild-type mice; the presence of an equivalent amount of proteins in the two types of sample loaded onto the gel is demonstrated by the signal obtained with an anti-β-tubulin (β-tub) antibody;

FIGS. 5 to 8 illustrate the alteration in the long-term depression (LTD) and in the long-term potentiation (LTP) in the STOP KO (−/−) mice;

FIG. 5 illustrates the basal synaptic response of the Schaffer collaterals: the "in/out"-type curves represent the slope of the curve of the excitatory post-synaptic potential (EPSP) as a function of the excitability of the fibers of the Schaffer collaterals, based on a section from wild-type mice (a) or from STOP KO (−/−) mice (b). Summary of the results obtained on six wild-type mice and six STOP KO (−/−) mice (c). The slopes of the curves are not significantly different, indicating normal basal synaptic transmission in the STOP KO (−/−) mice;

FIG. 6 illustrates the results of the experiments for long-term potentiation (LTP) at the synapses of the Schaffer collaterals and of the pyramidal cells of the CA1 region of the hippocampus:

FIG. 6(a) shows that a high frequency stimulation (tetanic stimulation induced by 4 stimuli of 100 Hz for 1 s, applied at intervals of 10 to 20 s) leads to a long-term increase in the slope of the EPSP curve, in a section from a wild-type mouse, FIG. 6(b) shows that, on the other hand, an identical stimulation leads to only a small increase in the slope of the EPSP curve in a section from a STOP KO (−/−) mouse, and FIG. 6(c) represents a summary of the results obtained in the wild-type mice and the STOP KO (−/−) mice. The initial values of the slopes of the EPSP curves were standardized in each experiment, using the mean value of the curve obtained during the control period (−10 to 0 min). The results, expressed as mean±s.e.m., correspond to the values obtained on 13 and 9 sections derived, respectively, from seven wild-type mice and six STOP −/− mice. These results show a significant deficiency in long-term potentiation in the STOP KO (−/−) mice (p=0.0007, measurement recorded after 30 to 40 minutes);

FIG. 7 illustrates the results of the experiments of long-term depression (LTD) at the synapses of the Schaffer collaterals and of the CA1 pyramidal cells:

FIG. 7(a) shows that low frequency stimulation (LFS, 1 Hz for 15 min) induces a long-term decrease in the slope of the EPSP curve in the sections from wild-type mice, FIG. 7(b) shows that, on the other hand, the low frequency stimulation does not induce a long-term decrease in the slope of the EPSP curve in the sections from KO −/− mice, and FIG. 7(c) represents a summary of the LTD experiments in the STOP KO (−/−) mice and in the wild-type mice. The results, expressed as mean±s.e.m., correspond to the values obtained on 15 and 9 sections of, respectively, nine wild-type mice and six STOP KO (−/−) mice. These results show a significant alteration in long-term depression (LTD) in the STOP KO (−/−) mice (p=0.01, results recorded after 40-45 minutes);

FIG. 8A illustrates the NMDA/AMPA ratio at the synapses of the Schaffer collaterals and of the CA1 pyramidal cells corresponding to the ratio of the values of the EPSP curves for the NMDA (N-methyl-D-aspartate) receptor and for the AMPA (alpha-amino-3-hydroxy-5-methyl-4-isoxazole propionic acid) receptor on 14 and 9 sections of, respectively, six wild-type mice and six STOP KO (−/−) mice. The slopes for the NMDA receptors and the AMPA receptors were measured for a stimulus strength corresponding to twice the threshold value. No significant difference was observed between the wild-type mice and the STOP KO (−/−) mice;

FIG. 8B illustrates the depolarization during a tetanic stimulation of the Schaffer collaterals: the graph represents the summary of the results of quantifying the depolarization during a tetanic stimulation. The depolarization is calculated 300 ms after the start of the first stimulus of 100 Hz. The experiments were carried out on 11 sections from wild-type mice and 8 sections from STOP KO (−/−) mice originating, respectively, from seven wild-type mice and six STOP KO (−/−) mice. The results are not significantly different in the wild-type mice and the STOP KO (−/−) mice;

FIG. 9 illustrates the alteration in synaptic plasticity in the short term in the STOP KO (−/−) mice:

FIG. 9A illustrates the results of the experiments of post-tetanic potentiation of the synaptic transmission of the Schaffer collaterals. A high frequency stimulation in the presence of the NMDA receptor antagonist D-APV (50-100 μM) induces a transient increase in the EPSP slope. The results were obtained using 6 and 10 sections originating, respectively, from four wild-type mice and five STOP KO (−/−) mice. The results show an alteration in the post-tetanic potentiation in the STOP KO (−/−) mice, (p=0.04, measurements carried out from 0 to 30 s after tetanic stimulation), FIG. 9B illustrates the results of the experiments of paired pulse facilitation (PPF) of the synaptic transmission of the Schaffer collaterals. The results obtained correspond to 7 and 12 sections originating, respectively, from four wild-type mice and five STOP KO (−/−) mice. The paired pulse facilitation is not significantly modified in the STOP −/− mice, and FIG. 9C illustrates the experiments of hippocampal mossy fiber frequency facilitation. The results were obtained using 10 and 12 sections obtained from 7 and 8 sections originating, respectively, from six wild-type mice and seven STOP KO (−/−) mice. In the wild-type mice, repeated stimulation of the synapses of the mossy fiber using stimulation frequencies of between 0.033 and 1 Hz caused a reversible 3-fold increase in the amplitude of the response of the mossy fiber. The facilitation is significantly altered in the STOP KO (−/−) mice (p=0.03, values recorded at a stimulation frequency of 1 Hz);

FIG. 10 illustrates the disorders of maternal behavior of the STOP KO (−/−) mice:

FIG. 10a: the survival of the newborns, derived from primiparous mothers, carrying the wild-type or mutated (STOP −/−) STOP allele is analyzed on the second day after birth;

FIGS. 10b and 10c: the manifestation of a maternal behavior is analyzed in the STOP KO (−/−) young primiparous females and young males, compared with the wild-type mice. The results are expressed in the form of mean±s.e.m.; n=9 for the wild-type and STOP KO (−/−) female mice and n=10 for the wild-type and STOP KO (−/−) male mice;

FIG. 11 illustrates the behavioral disorders in the STOP KO (−/−) mice; the activities of the mice (sleeping, eating, grooming, walking and remaining immobile while awake) were recorded on video for a period of 3 hours, n=11 for the wild-type mice (wt for wild-type) and the STOP KO (−/−) mice:

FIG. 11a: time given to each activity. Each box corresponds to a different activity, as indicated in the left-hand panel. The STOP KO (−/−) mice spend more time walking and remaining mobile than the wild-type mice, to the detriment of the time spent sleeping or eating;

FIG. 11b: number of changes in activity. Compared to the wild-type mice, the STOP KO (−/−) mice show a higher number of activity changes, with a higher number of walking and resting phases;

FIG. 11c: percentage of phases of grooming followed by a sleeping phase (GS) out of total number of sleeping phases (S) expressed as mean±s.e.m. The percentages are calculated for each mouse before calculating the mean. The G-S sequence which is typical in the wild-type mice is frequently interrupted in the STOP KO (−/−) mice;

FIG. 12 illustrates the state of anxiety of the STOP KO (−/−) mice, evaluated by the light/dark test. FIG. 12a: time spent in the lit box, and FIG. 12b: the number of passages between the two boxes are respectively recorded over a period of 5 minutes, from the first time the animals enter the box in darkness. The wild-type mice (+/+) are used as controls. The values correspond to mean value standard error of the mean (s.e.m). The differences between the KO mice and the control mice are indicated with a risk of p<0.01 (**);

FIG. 13 illustrates the short-term memory disorders of the STOP KO (−/−) mice, evaluated by the object recognition test. The wild-type mice (+/+) are used as controls. The results are expressed by the recognition index (RI): RI values significantly greater than 50% correspond to a positive recognition test. The values correspond to the mean value±standard error of the mean (s.e.m);

FIG. 14 illustrates the social behavior of the STOP KO (−/−) mice; the wild-type mice (+/+) are used as controls: FIG. 14a: evaluation of the time spent by a male in social investigation with respect to an intruder [n=11 for the wild-type mice and n=13 for the STOP KO (−/−) mice]; FIGS. 14b and 14c: inter-male aggression; the aggression tests are performed for two consecutive days [n=11 for the wild-type mice and n=10 for the STOP KO (−/−) mice]; the number of attacks and the time spent fighting (mean±standard error of the mean (s.e.m)) are recorded on the second day; *: p<0.05, **: p<0.01, Mann-Whitney U test;

FIG. 15 illustrates the effect of neuroleptics on the maternal behavior of the STOP KO (−/−) mice:

FIG. 15A: reinstallation in the nest of the newborns derived from wild-type (wt) and STOP KO (−/−) post-partum females. The reinstallation of the young mice to the nest was tested during the first day post-partum, in the mice treated with neuroleptics (mixture of haloperidol and chlorpromazine) or an anxiolytic (diazepam) or in untreated mice. The mice received a dose of 0.5 mg/kg/day from 6-8 days before birth until the day of birth. The females were placed in the presence of 3 newborns and the reinstallation in the nest was recorded for each female. The mean of the values obtained is given for each genotype (mean±s.e.m., n=6 for each group of wild-type and STOP KO (−/−) mice. * p<0.05,  p<0.02, * p<0.01, nonparametric Mann and Whitney U test;

FIG. 15B: survival of the newborns among the wild-type mice and the STOP KO (−/−) mice. The survival of the newborns is analyzed among the STOP KO (−/−) mice subjected to various treatments. The newborns are considered to be survivors when they are raised until weaning. No survival of the newborns was observed among the untreated STOP KO (−/−) mice (n=20) or the STOP KO (−/−) mice treated in the short term (FIG. 15A). On the other hand, survival of the newborns is observed in four of the seven STOP KO (−/−) mice treated in the long term (4 months) with neuroleptics. Survival of the newborns is observed in all the wild-type mice (n=7) given the same long-term treatment with neuroleptics. * p<0.05, ** p<0.02, * * * p<0.01, Fisher exact test.

EXAMPLE 1

Establishment of Knock-out (KO) Mice in which the STOP Gene is Inactivated: STOP KO (−/−) Mice 1—Materials and Methods
1-1 Construction of the Genomic Homology Fragment and of the Homologous Recombination Vector (Screening Vector)

The genomic DNA fragments used to construct the homologous recombination vector are derived from a genomic DNA library from mice of the strain 129, cloned into the P1 phage, and screened by hybridization with a cDNA of the STOP gene or a cDNA probe for said gene (Eric Denarier et al., BBRC, 1998, mentioned above).

The genomic homology fragment of the STOP gene is constructed from the 7.2 kb clone, the sequence of which is given in FIG. 2, according to the following steps: a 1012 pb fragment, containing the repeat sequences of the coding region of the STOP gene, which extends from positions 4118 to 5131 of the sequence given in FIG. 2, was deleted and replaced with an expression cassette containing the neomycin (neo) resistance gene under the control of the PGK promoter and the β-galactosidase (lacZ) gene under the transcriptional control of the endogenous STOP promoter. In addition, an EcoRV site was introduced in a 5' position of the lacZ gene.

The homologous recombination vector (ptSTOP) is obtained by cloning the homology fragment of the STOP gene described above into the vector pGK-TK. The vector pGK-TK derives from the vector pPNT constructed by Tybulewicz et al. (Cell, 1991, 65, 1153-1163) by insertion of the herpes simplex virus (HSV) thymidine kinase gene under the control of the phosphoglycerate kinase (PGK) promoter.
1-2 Homologous Recombination in ES Cells and Genotyping The vector ptSTOP is linearized with the Not1 enzyme and electroporated into ES cells (ES-R1, A. Naguy et al., PNAS, 1993, 90, 8428-8428) or into ES-AT1 cells isolated from 3.5-day blastocysts derived from F1 mice (129 Sv Pas×129 Sv Pas). Next, the electroporated ES cells are seeded onto a layer of neomycin-resistant fibroblasts pretreated with mitomycin, and cultured in DMEM medium rich in glucose (IN-VITROGEN) containing 15% of fetal calf serum and 1 000 IU/ml of leukemia inhibiting factor (Esgron, CHEMICON). Two days after transfection, geneticin (G418, INVITROGEN) is added to the culture medium, at the final concentration of 250 µg/ml. Gancyclovir (SYNTEX) is added from the fourth to the eighth day after transfection. The recombinant ES cell clones are removed 10 days after transfection and amplified before being frozen or analyzed. The genotype of the clones resistant to G418 and to gancyclovir is verified by Southern blotting analysis of the genomic DNA digested with EcoRV and hybridized with a probe specific for the STOP gene, located in the 5' region flanking the homologous recombination region (see FIG. 3) and corresponding to positions 698-1875, after EcoRV-EcoRI digestion, of FIG. 3. The size of the restriction fragments is 8 kb for the wild-type allele and 5.3 kb for the mutated allele (FIG. 1B).
1-3 Microinjection of the Recombinant ES Cells and Production of Transgenic Mice Homozygous for the Mutated Allele of the Stop Gene [Stop KO (−/−) Mice]

The recombinant ES cells carrying the mutated allele are microinjected into OF1 mouse embryos at the morula stage, and the injected embryos are then reimplanted into the uterus of the surrogate mother, so as to produce chimeric mice (Gene targeting: A practical approach, A. L. Joyner Ed., New York, Oxford University Press, 1993, pages 174-179). Crossing these chimeras with BalB/c or 129/sv mice (Laboratoires CHARLES RIVER) produces heterozygous F1 descendants in which the transmission of the STOP gene mutation is verified by Southern blotting analysis of the genomic DNA originating from a tail sample. The F1 descendants are crossed with one another to give homozygous F2 descendants.
1-4 Western Blotting Analysis of the Expression of the STOP Gene in the Brain of the STOP KO (−/−) Mice Extracts of brains from STOP KO (−/−) mice and from wild-type mice are prepared and analyzed by Western blotting using the polyclonal antibody 23C, according to the protocols described in Guillaud et al., mentioned above.
1-5 Histological Analysis, Immunolabeling of the Stop Proteins and Detection of the β-Galactosidase Activity of the Brain of the STOP KO (−/−) Mice
a) Histological Analysis 10- to 12-week-old wild-type and STOP KO (−/−) male mice are perfused with a solution of paraformaldehyde (4% PFA). The brains are fixed in the same solution for 2 h at 4° C. A cytochrome oxidase detection assay (Y. Liu et al., J. Neurosci. Methods, 1993, 49, 181-184) and staining with crystal violet are carried out on 100 µm sections of the brains.
b) Immunolabeling of the STOP Proteins The brains are prepared as described in paragraph a) and are then frozen in sucrose (20% in PBS). 20 µm brain sections are incubated successively in the following solutions: 1% $H_2O_2$ (15 min), 3% of BSA (30 min), and a mixture of the polyclonal antibody 23C (100 µg/ml) and of the peroxidase-coupled anti-rabbit antibody conjugate (overnight), and then the STOP proteins are revealed with ethylcarbazole (AEC, DAKO).
c) Detection of the β-galactosidase Activity Brain sections (100 µm) are fixed in 0.2% glutaraldehyde and 2% formaldehyde. The β-galactosidase activity is detected by staining the sections in a solution of PBS containing 5 mM of potassium ferricyanide, 5 mM of potassium ferrocyanide, 2 mM of magnesium chloride and 1 mg/ml of X-Gal, at 30° C. for 3 to 5 hours.
1-6 Analysis of the Microtubule Stability in the Neurons and the Glial Cells of the STOP KO (−/−) Mice Neurons and glial cells from embryos of wild-type and of STOP KO (−/−) mice are kept at ambient temperature or subjected to a temperature of 0° C. for 45 minutes. After extraction of the free tubulin, according to the protocol described in Laurent Guillaud et al., mentioned above, the microtubules are stained with an anti-tubulin antibody and the nuclei are stained with Hoechst solution.
2—Results
2-1 Establishment of STOP KO (−/−) Mice The genotypic profile of the STOP KO (−/−) homozygous mutant shows the presence of a 5.3 kb fragment (FIG. 1B) which indicates the deletion of the 1012 bp fragment containing the repeat sequences of the coding region of the STOP gene.

The analysis of the various heterozygous crosses shows that the mutated STOP allele is transmitted in a mendelian manner.

The STOP KO (−/−) homozygous mice are viable, appear to be in good health, and exhibit no visible macroscopic lesions.

A null phenotype is obtained; the mice carrying the mutated allele in the homozygous state do not express any STOP protein:

- the analysis of the brain extracts from the STOP KO (−/−) mice, by Western blotting using the polyclonal antibody 23C (Guillaud et al., mentioned above), shows an absence of STOP proteins (E-STOP and N-STOP) in these mice, whereas these two isoforms are detected in the wild-type adult mice (FIG. 4);
- the immunohistological analysis of the brain sections from the STOP KO (−/−) mice shows an absence of specific labeling of the STOP proteins (E-STOP and N-STOP) in these mice, whereas specific labeling of these STOP proteins is observed in all the nervous tissues of the wild-type adult mice.

2-2 Lack of Stability with Respect to Cold of the Microtubules of Cells Derived from STOP KO (−/−) Mice Due to the absence of STOP protein in the STOP KO (−/−) mice, depolymerization of the microtubules is observed simultaneously after exposure to cold, in the neurons, glial cells and the fibroblasts.

2-3 Absence of Anatomical Lesions in the Brain of the STOP KO (−/−) Mice

Analysis by optical microscopy of the anatomy of the brain of the STOP KO (−/−) mice, using parasagital sections stained with crystal violet to visualize the nuclei, shows no differences between the KO −/− mice and the wild-type mice.

More precisely:

- analysis of the layers of cells of the cerebellum, of the neocortex, of the hippocampus and of the olfactory bulb, which correspond to those showing considerable expression of the STOP proteins in the wild-type mice, shows a completely normal organization in the KO −/− mice,
- examination of the somatosensory cortex, using tangential sections stained to reveal the cytochrome oxidase activity, showed a normal organization of the barrel fields in the KO −/− mice,
- the β-galactosidase expression profile in the brain of the STOP KO (−/−) mice is identical to that observed in the heterozygous mice, which demonstrates that the cells which, in the normal state, express considerable amounts of STOP proteins are still present in the STOP −/− mice.

The STOP (−/−) homozygous mice which do not exhibit anatomical brain lesions detectable by microscopy exhibit, however, behavioral disorders.

EXAMPLE 2

Electrophysiological Analysis of the Synaptic Transmission of the KO STOP −/− Mice 1—Materials and Methods To prepare the sections of hippocampus, 1- to 3-month-old mice were deeply anesthetized with nembutal. Brain sections (300-400 µm) were prepared in an artificial cerebrospinal fluid (124 mM NaCl, 26 mM NaHCO$_3$, 2.5 mM KCl, 1.25 mM NaH$_2$PO$_4$, 2.5 mM CaCl$_2$ and 1.3 mM MgCl$_2$), at a temperature of between 4° C. and 8° C. More precisely, the sections were maintained at ambient temperature for at least 1 h and were then submerged in a chamber containing artificial cerebrospinal fluid equilibrated with 95% O$_2$ and 5% CO$_2$, and transferred into a superfusion chamber.

The excitatory post-synaptic potential (EPSP) of the extracellular fields was recorded using microelectrodes (1 to 3 MΩ) filled with artificial cerebrospinal fluid. The measurements were carried out at a temperature of approximately 22 to 25° C. Bipolar steel electrodes were used to stimulate the Schaffer collateral and the mossy fiber (stimulation of 10 to 100 mA, for 0.1 ms with intervals of 10 to 30 s between each stimulation).

For all the analyses carried out in the CA1 region, the stimulating electrodes and the extracellular measuring electrodes were placed in the stratum radiatum, and picrotoxin (final concentration of 100 µM, SIGMA) was added to the artificial cerebrospinal fluid. In these series of analyses, the CA1 region was separated from the CA3 region by sectioning the brain section with a knife before measurement.

For the in/out-curves, the excitability of the fibers was analyzed after blocking the activation of the glutamate receptor with the AMPA (alpha-amino-3-hydroxy-5-methyl-4-isoxazole propionic acid) receptor antagonist NBQX (5 to 10 µM, TOCRIS). The responses of the AMPA receptor were measured and then the responses of the NMDA (N-methyl-D-aspartate) receptor were revealed after suppression of the extracellular magnesium and isolated by adding NBQX (10 µM), in order to perform a quantitative analysis.

For the post-tetanic potentiation (PTP)-type analyses, a high dose of D-APV (50 to 100 µM; provided by TOCRIS) was added to the solution of the bath, at least 10 minutes before the tetanic shock.

For the paired pulse experiments, the Schaffer collaterals were stimulated repeatedly with two stimuli of the same strength separated by short intervals of varying duration. The result is expressed by the ratio between the amplitude of the response to the second stimulus and to the first stimulus, determined from an average of 15 to 20 responses, for each value of the interval.

The responses of the mossy fibers were analyzed by applying a bath of the selective glutamate receptor agonist DCG IV (type 2 metabotropic group). The inhibitory effects of the DCG IV (10 mM, provided by TOCRIS) on the entries into the mossy fibers are similar in the wild-type mice and the STOP KO (−/−) mice. NBQX (5 to 10 mM) was applied at the end of each analysis of the mossy fiber, in order to determine the excitability of these fibers.

The data acquisition and the analysis of the long-term potentiation (LTP) and long-term depression (LTD) experiments were carried out blind, relative to the genotype of the mice. All the results are expressed in the form of mean±standard error of the mean (s.e.m).

2—Results

The functioning of the synapses of the STOP KO (−/−) mice was analyzed in the hippocampus, where there is considerable expression of the STOP proteins.

First of all, in order to selectively analyze glutamatergic transmission, the synaptic transmission in the CA1 region of the hippocampus was analyzed in the presence of picrotoxin, a GABA type A receptor antagonist.

The basal synaptic transmission was evaluated by analyzing the relationship between the excitability of the fibers of the Schaffer collaterals and the amplitude of the excitatory post-synaptic potentials in the CA1 region of the hippocampus. The analysis was carried out for various stimulation strengths. The in/out-type curves are qualitatively similar in the STOP KO (−/−) mice and the wild-type mice (FIGS. 5a and 5b). The quantitative analysis carried out on the slopes of the in/out curves of six wild-type mice and six STOP KO (−/−) mice shows no difference between the 2 groups of mice (FIG. 5c), indicating normal basal synaptic transmission in the STOP (−/−) mice.

For the analysis of the synaptic plasticity, the synaptic response to a standard stimulus was evaluated by the slope of the EPSP curve. The basal values of the slopes are determined by repeat low-frequency stimulations (0.03-0.1 Hz). At time zero, a conditioning stimulation protocol is applied. The synaptic adaptation is demonstrated by a stable deviation of the values of the EPSP slopes, compared to the basal values.

A high-frequency (100 Hz) conditioning protocol, applied to the Schaffer collateral-pyramidal cell of the CA1 region synapse, produces a stable increase in the slopes of the curves, in the sections from the wild-type mice (FIG. 6a), indicating synaptic potentiation in these mice. This potentiation persisted for more than 30 minutes, and such a persistence represents a long-term potentiation (LTP).

In the STOP KO (−/−) mice, a weaker potentiation of the synaptic transmission is observed (FIG. 6b).

This difference is confirmed by the quantitative analysis of all the results obtained in the 2 groups of mice (FIG. 6c).

The long-term depression (LTD) was analyzed at the same synapses of the Schaffer collaterals and of the CA1 pyramidal cells. The conventional low-frequency stimulation protocol was used (LFS, 900 stimulations of 1 Hz). Sections from STOP KO (−/−) mice showed a significant decrease in the LTD amplitude (FIG. 7b).

These results show that the LTP and the LTD are altered in the STOP KO (−/−) mice.

The LTP and the LTD depend crucially on the activity of the NMDA receptor. However, the basal activity of the NMDA receptor, measured by the ratio of the NMDA/AMPA response to stimuli (FIG. 8A), and the activation of the NMDA receptor during the tetanic stimulation (FIG. 8B) are comparable in the STOP KO (−/−) mice and the wild-type mice.

These results demonstrate a deficiency in the 2 major forms of synaptic plasticity (LTP and LTD) in the STOP KO (−/−) mice and indicate that this deficiency is not linked to a deficiency in expression of the NMDA receptor in the STOP KO (−/−) mice.

FIG. 9B shows that, in the STOP KO (−/−) mice, the synaptic potentiation is altered during the first minutes after tetanic stimulation, and also at later times. Consequently, the existence of a possible deficiency in short-term plasticity, at the synapses of the Schaffer collaterals and of the CA1 pyramidal cells was analyzed by measuring post-synaptic potentiation (PTP) and paired pulse facilitation (PPF). Like LTP, PTP is a form of potentiation subsequent to a tetanic stimulation (stimulus of 1 Hz for 1 s), but it is induced in the presence of the NMDA receptor antagonist (D-APV) in order to block post-synaptic events involved in LTP, and persists only for a few minutes, subsequent to the tetanic stimulation. PPF is another form of synaptic plasticity observed when the synapses are stimulated by paired pulses. PPF is defined by an increase in the synaptic response in response to the second stimulus. The PTP is reduced in the STOP KO (−/−) mice (FIG. 9A). On the other hand, the paired pulse facilitation (PPF) is similar in the wild-type mice and the STOP KO (−/−) mice (FIG. 9B), for an extended range of decreasing values of extracellular calcium concentration.

The synaptic plasticity at the synapses of the mossy fibers and of the pyramidal cells of the CA3 region was then analyzed. No difference in the long-term potentiation (LTP) nor in the paired pulse facilitation (PPF) was observed between the STOP KO (−/−) mice and the wild-type mice. In order to study the short-term plasticity, the mossy fibers were stimulated with increasing frequencies ranging from 0.033 to 1 Hz. This protocol normally induces a considerable and transient increase in the amplitude of the response of the mossy fibers, a phenomenon known as frequency facilitation. The amplitude of the frequency facilitation was significantly decreased in the STOP KO (−/−) mice, in comparison with the wild-type mice (FIG. 9C).

All of these results show that several distinct forms of long-term and short-term plasticity are altered in various regions of the hippocampus, in the STOP KO (−/−) mice.

EXAMPLE 3

Analysis of the Behavioral Disorders of the STOP KO (−/−) Mice

1—Materials and Methods

All the behavioral tests were carried out on litters of STOP KO (−/−) mice and of control wild-type mice derived from the same colony (genetic background BALBc/129 Sv).

1-1 Maternal Behavioral Tests (Mothering)

The maternal behavior is assessed by the performing of the following acts:
1. preparing a nest
2. reinstalling the newborns in the nest.

Tests Carried Out in Nulliparous Females and in Males

Young nulliparous females, 28 to 49 days old, were reared individually for at least one day before the beginning of the experiment, and they were then provided with cotton to construct a nest.

On D1, each female is placed together with 3 1- to 3-day-old newborns in the following way: the newborns are each placed in one of the corners of the cage, at a distance from the nest, and, after 30 minutes, the newborns are returned to their natural mother.

On D2, each female is again placed together with the newborns and, for each female, the number of young mice reinstalled in the nest is evaluated for a period of 30 minutes.

Young males, 30 to 45 days old, were used under the same conditions as the nulliparous females, with the only difference that they were placed together with the young mice for 2 consecutive days before being tested on D3, instead of D2 for the nulliparous females.

Tests Carried Out in Primiparous or Multiparous Mothers

Post-partum females (second gestation) were reared individually from the beginning of their gestation. On the day of giving birth, the young mice were removed and kept in the warm for one hour. The mother was then removed from her usual cage and three newborns were each placed in a corner of this same cage, at a distance from the nest. Next, the mother was returned to her nest and the number of young mice reinstalled in the nest, over a period of 20 minutes, was evaluated.

1-2 "Light/Dark Test"

The test of the choice between light and dark, known as "light/dark test", is used to reveal a state of anxiety caused by an anxiety-generating stimulus. This method, validated by Misslin et al. (1990, *Neuroreport, I,* 267-270), is based on the natural tendency of rodents to prefer a dark environment, and makes it possible to evaluate the emotional response of animals subjected to a stress consisting of light.

The animals are maintained in individual cages placed in an incubator having a temperature of between 21° C. and 22° C. and an inverted light/dark cycle of 12 h/12 h, with as much water and food as desired. All the experiments are carried out in accordance with the institutional directives relating to animal experimentation.

The device consists of two polyvinylcarbonate boxes (20 cm×20 cm×14 cm) covered with perspex. One of the boxes is made dark and the other is lit using a 100 W desk lamp placed at a distance of 15 cm (4400 1x). An opaque plastic tunnel (5 cm×7 cm×10 cm) separates the darkened box from the lit box.

The animals are individually placed in the lit box with the head directed toward the tunnel. The time spent in the lit box (TLB) and the number of passages between the two boxes are recorded over a period of 5 minutes, from the first time the animals enter the darkened box.

The overall analysis of the results is carried out using the Mann and Whitney U test. The risk (p) is fixed at p<0.05. The results are expressed by the mean value±standard error of the mean (s.e.m).

1-3 Object Recognition Test

The short-term memory is evaluated by the object recognition test previously described (Ennaceur et al., 1988, *Behav. Brain Res.*, 31, 47-59; Dodart et al., 1997, Neuroreport, 8, 1173-1178), which is based on the natural tendency of rodents to explore a new object, in preference to a familiar object.

The animals are maintained under the conditions as described in example 3, section 1-2.

The object recognition test is carried out in an open space made of perspex (52 cm×52 cm×40 cm). The floor is divided into 9 squares of equal size. The objects to be distinguished are a bead and a dice. The animals are given 30 min to become familiar with the open area.

The following day, they are subjected to a learning test of 10 min (first test) during which they are individually placed in the open space, in the presence of an object A (dice or bead). During this period, the following are recorded:
  the locomotor activity, evaluated by the number of squares crossed, and
  the time spent by the animal in exploring object A, i.e. the time during which the animal's nose is directed at a distance from the object of less than 1 cm.

Three hours later, they are subjected to a recognition test of 10 min (second test). For this test, object A and the other object (B) are placed in the open space and the locomotor activity, and also the amount of time spent exploring object A ($t_A$) and object B ($t_B$), are recorded. Next, the recognition index (RI, on the Y-axis in FIG. 13) is calculated from the following formula $RI = t_A/(t_A + t_B) \times 100$. A recognition test is considered to be positive if the value of the recognition index is significantly greater than 50%.

The overall analysis of the results is carried out as described in example 3, section 1-2.

1-4 Social Behavior Test, Intruder Test 1-4-1 Social Investigation

The social behavior is evaluated on young males, 4 weeks old, isolated for one week in a cage (resident young males); a male intruder reared in a group is introduced into the cage and the social investigation time (approach, sniffing, sexual posturing) of the resident young males is evaluated for 6 minutes. The results are analyzed using the Mann and Whitney U test. The results are expressed by the mean value±standard error of the mean.

1-4-2 Inter-male Aggression

Resident males are isolated for one month and an intruder (male reared in a group) is placed in the cage. The number of attacks and the time spent fighting by the residents is measured over a period of 5 minutes. The results are analyzed using the Mann and Whitney U test. The results are expressed by the mean value±standard error of the mean.

2—Results 2-1 Maternal Behavior of the STOP KO (−/−) Mice

The STOP KO (−/−) mice exhibit major deficiencies in maternal behavior which result in a complete lack of interest for their progeny, as shown by the results given in FIG. 10, obtained from 161 young mice derived from 20 female STOP KO (−/−) mice crossed with heterozygous males:

all the newborns, derived from primiparous STOP KO (−/−) mothers die within 24 h following birth due to lack of attention from the mother (FIG. 11a), whatever their genotype (genetic background BALBc/129Sv or 129Sv). By comparison, a 93% survival rate is observed in the newborns derived from a primiparous mother carrying the wild-type allele in the homozygous state [(+/+) wild-type mice], which exhibit normal maternal behavior comprising, in particular, preparation of a nest and reinstallation of the young mice in the nest (FIG. 11a). It was also shown that the maternal behavior of the STOP KO mice was not improved by repeated gestations (multiparous mothers);

the newborns of a STOP KO (−/−) mother are never cannibalized and they are raised until weaning when they are adopted by wild-type mothers, which demonstrates that the death of the young mice is directly linked to the genotype of the mother. To determine the causes of death, a deficiency in suckling at the teat associated with an absence of olfactory signal at the level of the teats of the STOP KO (−/−) females was investigated. When the young mice derived from a STOP KO (−/−) mother are left in the presence of their mother but repeatedly replaced in position to be mothered, through a human intervention, all the young mice show behavior consisting of searching for and attaching to the teat. The presence of this guided behavior indicates that the STOP KO (−/−) females possess the olfactory signals essential to suckling. In addition, under these conditions, the presence of milk in the stomach of the young mice was observed. These results demonstrate that the death of the young mice was not linked to lactation deficiencies in the STOP KO (−/−) mice;

the deficiency in reinstallation in the nest is not due to a deficiency in olfactory recognition of the young mice in the STOP KO (−/−) mice, given that the STOP KO (−/−) females placed close to their progeny sniff the young mice and, in addition, show normal behavior in an olfaction test (hidden food test);

in order to verify whether the deficiency in maternal behavior observed in the STOP KO (−/−) mice was associated with hormonal status, complementary tests were carried out in the nulliparous females and in the young males. The results of the "reinstallation in the nest" tests, carried out in these two groups of mice, show a deficiency in maternal behavior of the nulliparous female or male STOP KO (−/−) mice (FIGS. 10b and 10c).

All of these results indicate that the deficiency in maternal behavior observed in the STOP KO (−/−) mice is independent of an obvious organic deficiency and of the hormonal status of these mice, which indicates that there is only one manifestation of the multiple behavioral deficiencies observed in these STOP KO (−/−) mice.

2-2 Other Behavioral Disorders of the Stop KO (−/−) Mice

Although examination of the general condition of the STOP KO (−/−) mice reveals no apparent deficiency, they exhibit a strange behavior with phases of intense activity with no apparent purpose, accompanied by frequent changes in activity, occurring randomly. Occasionally, the mice exhibit a period in which they have an attack, of approximately 20 min, during which the animals turn in circles or dig in the cage, compulsively. These mice also go through periods of apparent prostration during which they remain immobile, do not sleep and do not react to the environment. Such attacks have never been observed in the wild-type mice and do not resemble epileptiform events. The acute attacks are difficult to study systematically, but they represent paroxysmal manifestations of a continuous background noise of behavioral abnormality. The video recording was used to evaluate the behavior of the mice quantitatively. The time spent by the mice in eating, sleeping, grooming, walking and remaining immobile while awake was measured for a period of 3 hours, and the results are given in FIG. 11a. Compared to the wild-type mice, the STOP KO (−/−) mice spend more time moving around in the cage or remaining immobile, although they are awake, to the detriment of the time spent feeding and sleeping. The mutant mice exhibit greater changes in activity, largely due to a significantly greater number of phases of movement without purpose and of phases of immobility (FIG. 11a). The changes in activity of the STOP KO (−/−) mice often break a period of characteristic activity. For example, in the wild-type mice, 71% of the sleep phases are preceded by a grooming phase with or without a tranquility phase being intercalated. The corresponding frequency in the STOP KO (−/−) mice is 47%, a value just above the expected background noise in the case of random sequences of activity (35%, FIG. 12a). These quantitative results confirm the impression of non-organized activity which is not directed toward a purpose, given by the observation of the STOP KO (−/−) mice.

Complementary analyses of the behavior of the STOP KO (−/−) mice were carried out using conventional tests.

State of Anxiety of the STOP KO (−/−) Mice

The STOP KO (−/−) mice are frightened by an anxiety-generating stimulus and the wild-type (+/+) mice have a normal behavior, as shown by the results of the light stimulation test (light/dark test) given in FIGS. 12a and 12b. In addition, it was shown, by prior tests, that the spontaneous locomotor activity of the mutant (−/−) mice was not modified compared to the wild-type (+/+) mice.

Short-term Memory of the STOP KO (−/−) Mice

Figure 1A:
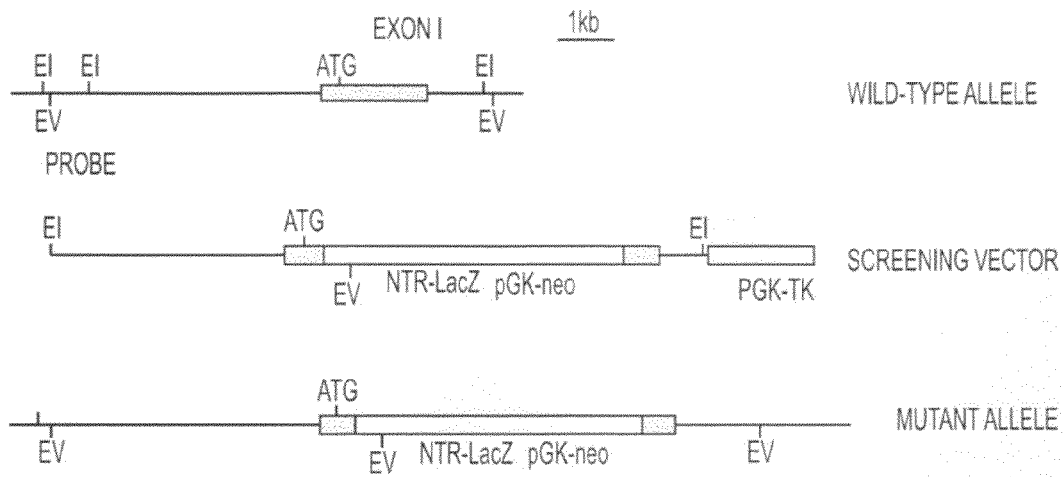
Figure 1B:
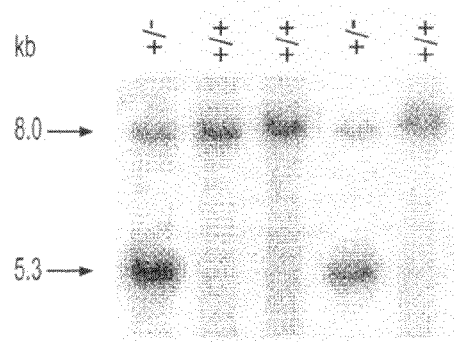
Figure 4:
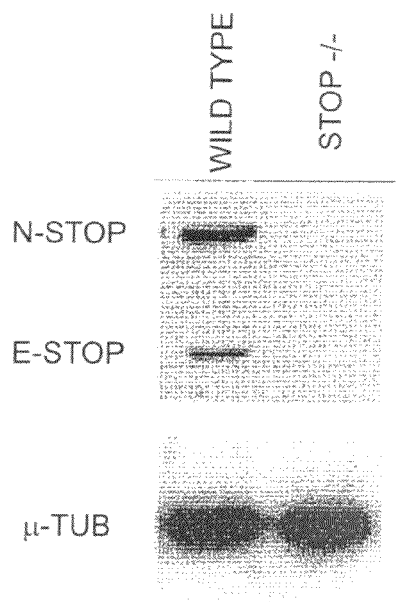
Figure 5B:
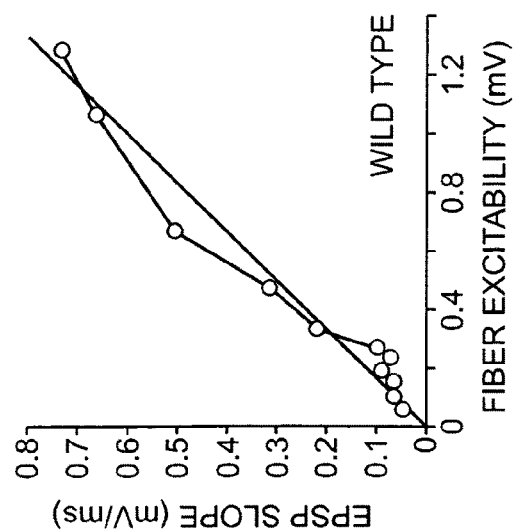
Figure 5A:
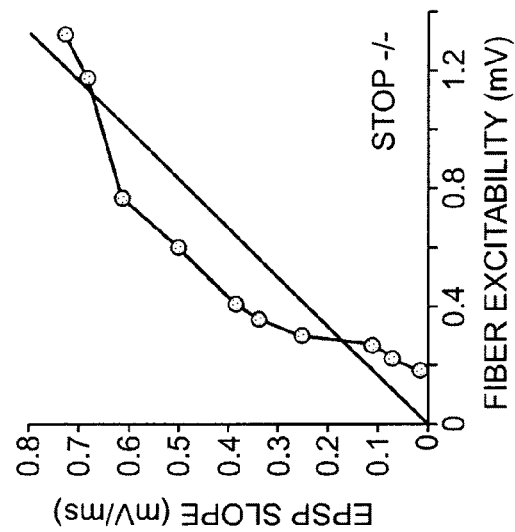
Figure 6A:
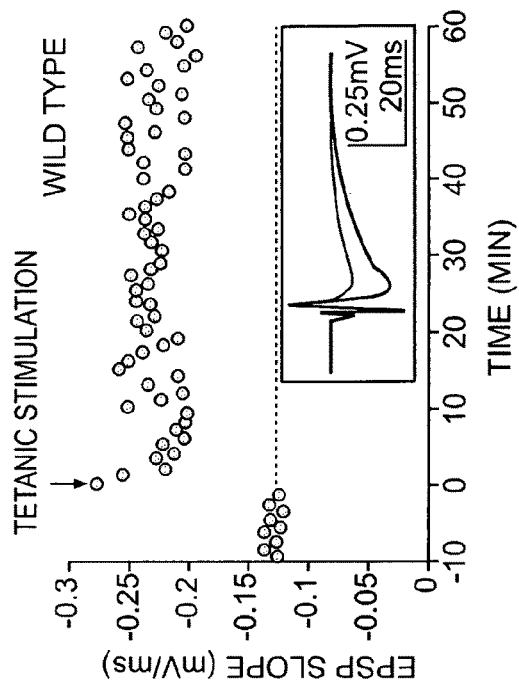
Figure 5C:
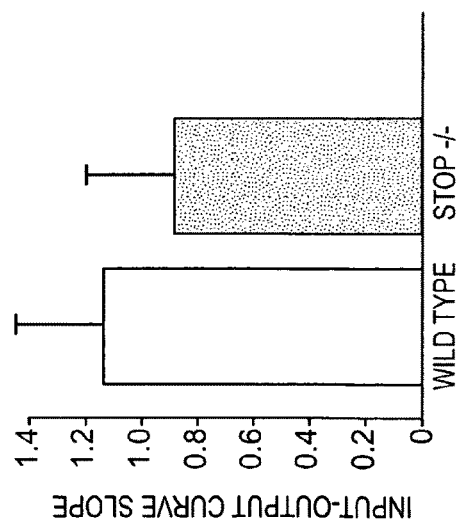
Figure 7A:
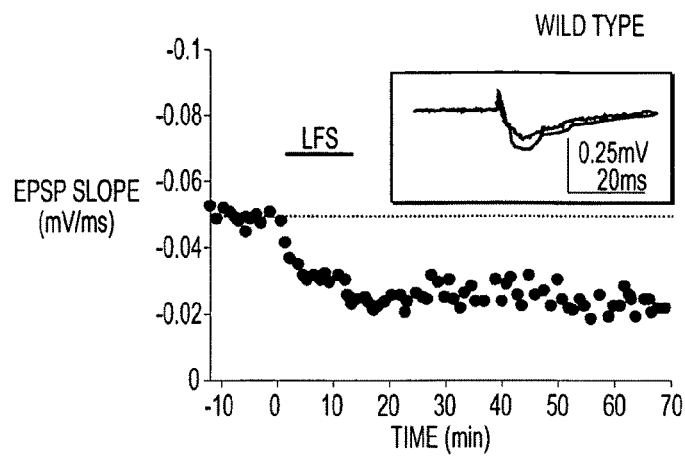
Figure 7B:
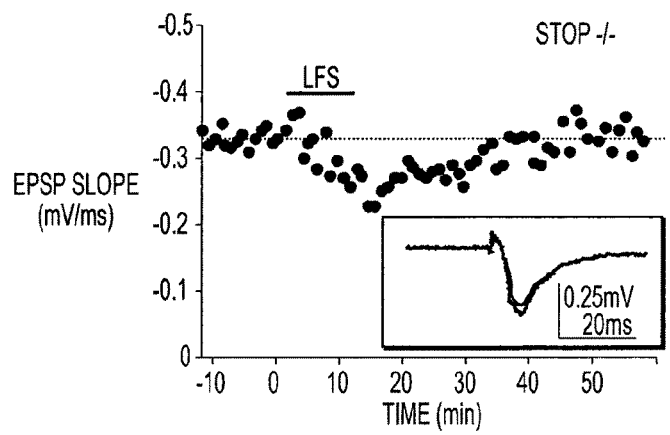
Figure 7C:
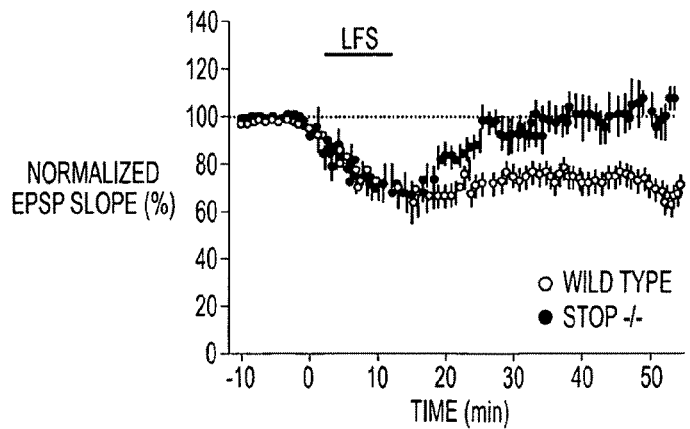
Figures 9A, 9B, 9C:
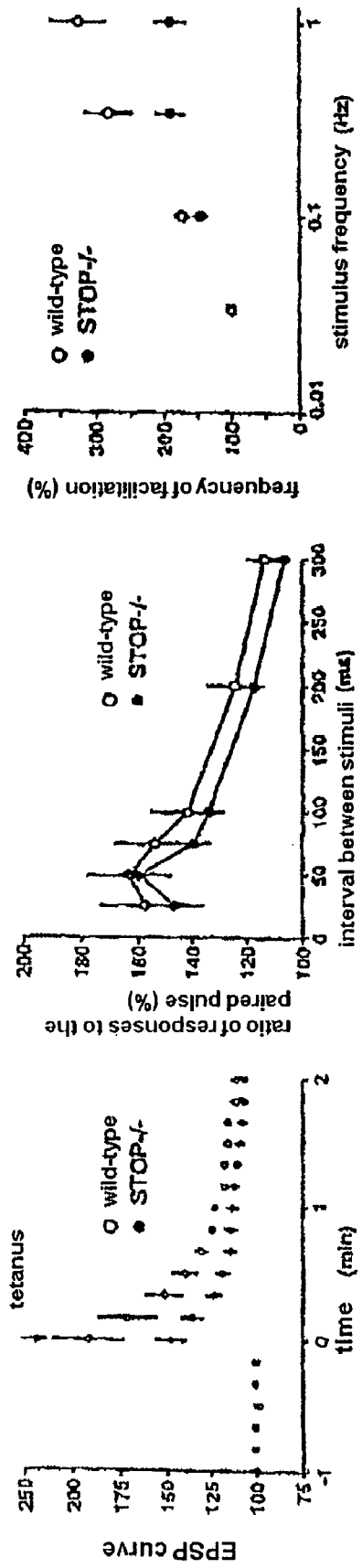
Figure 11A:
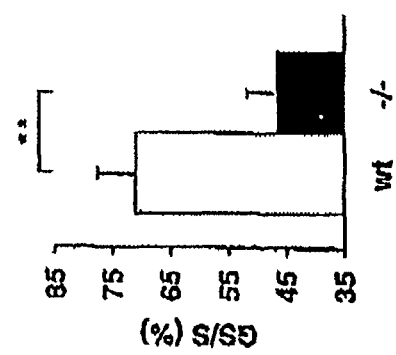
Figure 11B:
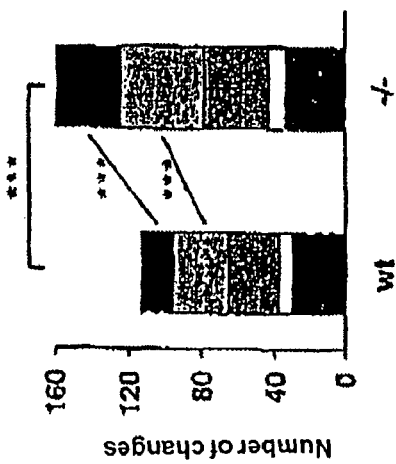
Figure 11C:
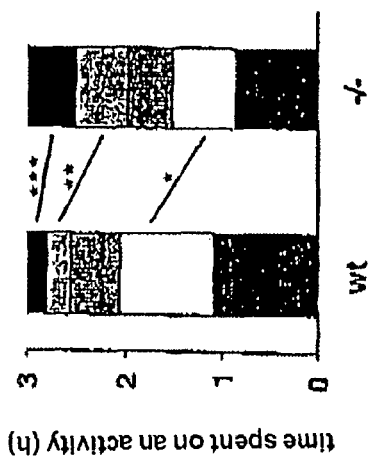
Figure 12A:
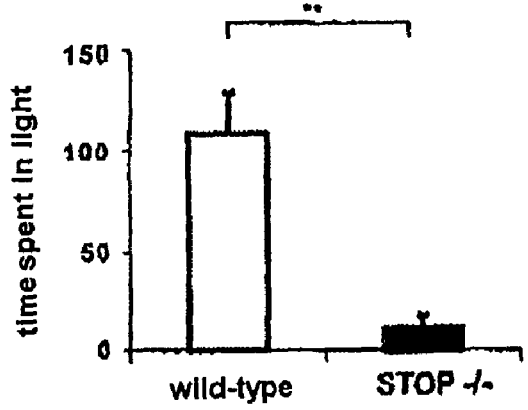
FIG. 12a shows that the wild-type (+/+) mice spend much more time in the lit box than the STOP KO (−/−) mice, which remain in the darkened box throughout almost the entire test. The differences observed between the KO (−/−) mice and the wild-type (+/+) mice are statistically significant: p<0.01, Mann and Whitney U test.
Figure 12B:
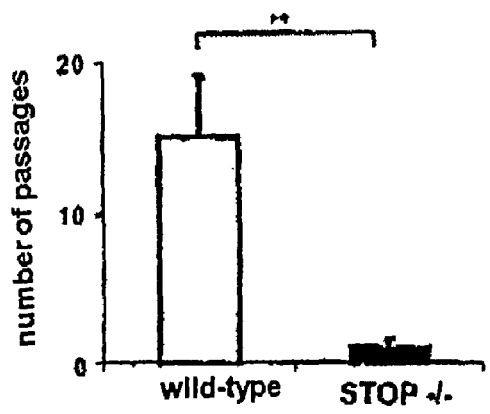
FIG. 12b shows that the wild-type mice enter the lit box more frequently than the STOP KO (−/−) mice. The differences observed between the STOP KO (−/−) mice and the wild-type (+/+) mice are statistically significant: p<0.01, Mann and Whitney U test.
Figure 13:
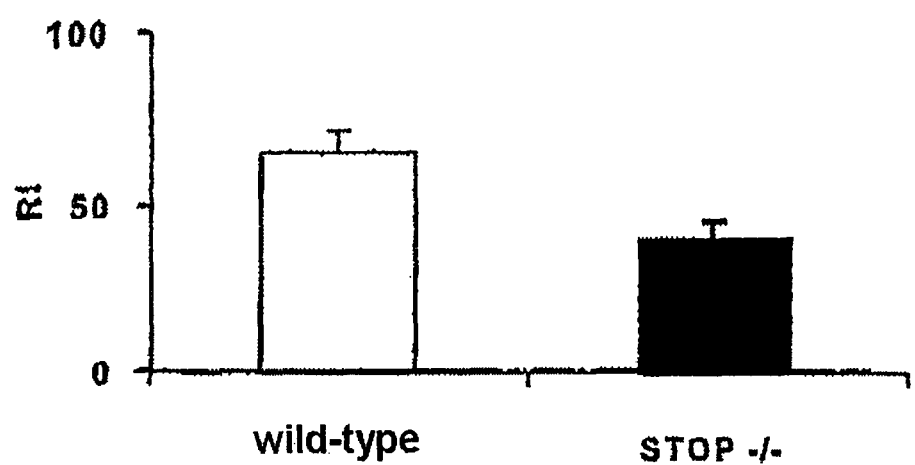

The STOP KO (−/−) mice exhibit short-term memory disorders, as shown by the results of the recognition test, given in FIG. 13:
  the recognition index, measured in the wild-type mice (65%) is significantly higher than the index of 50% observed in the STOP KO (−/−) mice (p=0.004 for the (+/+) mice, Student's test);
  the time spent exploring objects A and B, recorded during the second test (recognition test) shows that the wild-type mice explore the new object in preference to the familiar object;
  the STOP KO (−/−) mice explore neither of the objects during the two tests (learning and recognition). They move around in the open space but show no interest in the objects. This behavior might be explained by their state of anxiety, as shown by the results of the light/dark test. This state of anxiety is revealed in particular by the fact that the mice move along the walls and that they do not cross the open space, since they appear to be frightened by the environment and by the objects which represent an anxiety-generating stimulus.

Social Behavior

The STOP KO (−/−) mice exhibit disorders of social investigation (FIGS. 14a, 14b and 14c).

FIG. 14a shows that the time spent by the residents in exploring the intruder is significantly reduced when the resident is a STOP KO (−/−) male, (p<0.05).

FIG. 14b shows that, in the inter-male aggression test, the number of attacks carried out by the STOP KO (−/−) residents is less than the number of attacks carried out by the wild-type males (p<0.01).

FIG. 14c shows that the time spent fighting by the resident STOP KO (−/−) males is reduced in comparison to the wild-type males (p<0.01).

EXAMPLE 4

Effect of Anxiolytics and of Neuroleptics on the Maternal Behavior of the STOP KO (−/−) Mice 1—Materials and Methods The effect of anxiolytics (diazepam) and of neuro-leptics (chlorpromazine, haloperidol or clozapine) on the behavioral disorders of the STOP KO (−/−) mice was evaluated in the maternal behavior test as defined in example 3 ("reinstallation in the nest" test).

Haloperidol (Haldol$^R$, JANSSEN-CILAG), chlorpromazine (Largactil$^R$, RHONE-POULENC) and diazepam (Valium$^R$, ROCHE) were administered to the mice in the drinking water, at a dose of 0.5 mg/kg/day.

2—Results a) Short-term Treatment

The effect of short-term administration (for 6 to 8 days from the 6th day preceding the birth) of anxiolytics (diazepam) and of neuroleptics (chlorpromazine, haloperidol or clozapine) on the behavioral disorders of the STOP KO (−/−) mice was evaluated in the "reinstallation in the nest" test.

Figure 15A:
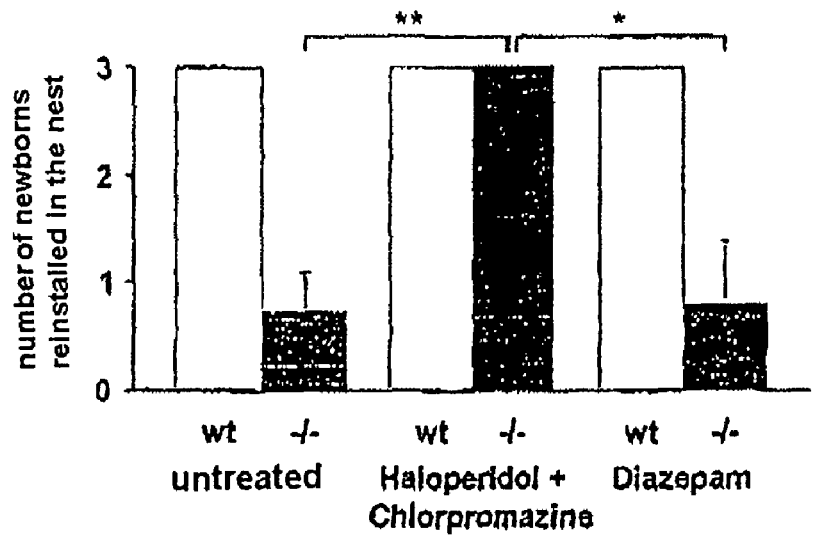

The reinstallation of the young mice in the nest is dramatically altered in the untreated STOP KO (−/−) mothers and is slightly improved by the administration of diazepam (FIG. 15A). On the other hand, the STOP KO (−/−) mothers treated with neuroleptics behave as well as the wild-type mice (FIG. 15A). However, no survival of the young mice was observed in either the treated or untreated STOP KO (−/−) mice. These results indicate a specific but limited beneficial effect of short-term administration of neuroleptics, on the behavior of the STOP KO (−/−) mice.

b) Long-term Treatment

Figure 15B:
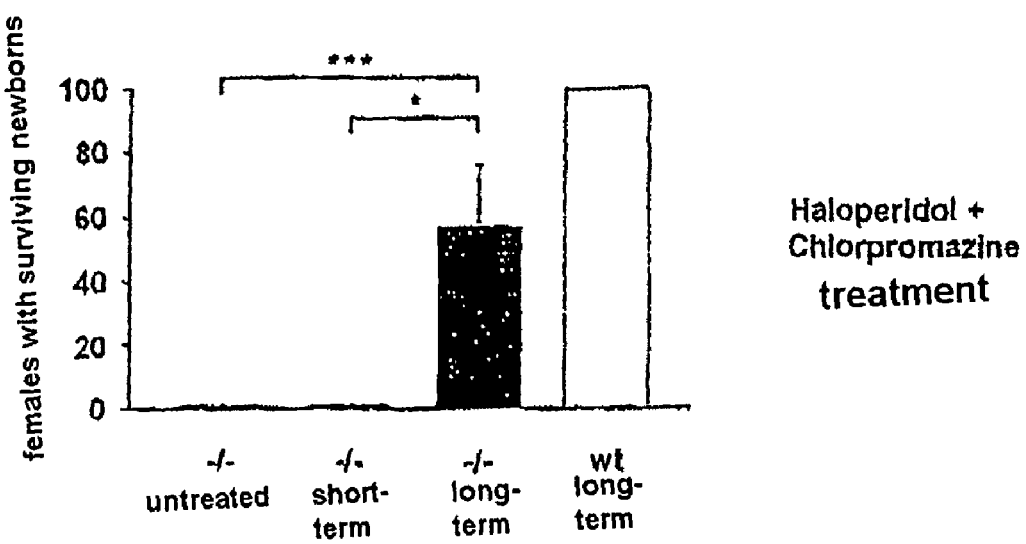

Seven STOP KO (−/−) mice and seven wild-type mice were given a daily administration of a mixture of chlorpromazine and haloperidol, for 4 months, starting from weaning and continuing during growth, coupling with males, gestation, birth and the post-partum period. The seven wild-type mice exhibited normal maternal behavior and all their young mice survived (FIG. 15B). Notably, in four of the seven STOP KO (−/−) mice, an improvement in the maternal behavior was sufficient to allow survival of the young mice, with survivor/newborn ratios of, respectively, 3/11, 4/8, 2/4 and 1/5 in these four mice.

The proportion of female STOP KO (−/−) mice with surviving young mice is significantly higher in the mice given long-term treatment with neuroleptics (4/7), compared to the untreated mice (0/20) or to the mice given short-term treatment with neuroleptics (0/6, FIG. 15B).

These results indicate that long-term administration of neuroleptics is capable of re-establishing a normal behavior in the STOP KO (−/−) mice, compatible with survival of the young mice.

As emerges from the above, the invention is in no way limited to its methods of implementation, preparation and application which have just been described more explicitly; on the contrary, it encompasses all the variants thereof which may occur to a person skilled in the art, without departing from the context or the scope of the present invention.

The invention claimed is:

1. A transgenic knockout mouse comprising a genome wherein both alleles of a gene encoding a Stable Tubulin Only Polypeptide Protein (STOP) are inactivated by deleting at least the nucleotides corresponding to the nucleotide positions between 4118 and 5131 of SEQ ID NO: 1, wherein said transgenic knockout mouse is a model for selecting or screening psychoactive products, and wherein said transgenic knockout mouse exhibits a lack of mothering, disorders of social investigation, an abnormal state of anxiety, and short-term memory disorders.

2. The transgenic knockout mouse of claim 1, wherein said inactivated alleles are obtained from a construct, said construct comprising a nucleic acid sequence derived from the same mouse or from a mouse that is different from the mouse into which said construct is inserted and wherein said construct is selected from the group consisting of: (i) constructs which do not comprise the region between nucleotide positions 4118 and 5131 of the genomic sequence SEQ ID NO:1 encoding a Stable Tubulin Only Polypeptide Protein (STOP) and (ii) constructs comprising 4.1 kb of the Stable Tubulin Only Polypeptide Protein (STOP) gene corresponding to the sequence consisting of nucleotides 1 to 4118 of SEQ ID NO:1, the gene encoding β-galactosidase, placed under the control of the endogenous Stable Tubulin Only Polypeptide Protein (STOP) promoter, a neomycin resistance gene under the control of the PGK promoter, 1.57 kb of sequence of the Stable Tubulin Only Polypeptide Protein (STOP) gene corresponding to the sequence consisting of nucleotides 5131 to 6701 of SEQ ID NO:1 and, finally, the thymidine kinase gene under the control of PGK promoter.

3. The transgenic knockout mouse of claim 2, wherein the constructs comprise a region of the Stable Tubulin Only Polypeptide Protein (STOP) promoter in combination with a reporter gene, said reporter gene being green fluorescent protein gene.

4. The transgenic knockout mouse of claim 1, wherein said mouse exhibits deficiencies in synaptic plasticity.

5. The transgenic knockout mouse of claim 1, wherein said mouse does not exhibit anatomical brain lesions detectable by microscopy.

6. A transgenic knockout mouse comprising a genome wherein both alleles of a gene encoding a Stable Tubulin Only Polypeptide Protein (STOP) are inactivated by deleting at least the nucleotides corresponding to the nucleotide positions between 4118 and 5131 of SEQ ID NO:1, wherein said transgenic mouse is a model for selecting or screening psychoactive products, and wherein said transgenic mouse exhibits a lack of mothering; disorders of social investigation consisting of (i) a reduction in the amount of time spent exploring an intruder, (ii) a decrease in the number of inter-male attacks, and (iii) a decrease in the amount of time spent fighting; an abnormal state of anxiety; and short-term memory disorders.

7. A transgenic knockout mouse comprising a genome wherein one allele of a gene encoding a Stable Tubulin Only Polypeptide Protein (STOP) is inactivated by deleting at least the nucleotides corresponding to the nucleotide positions between 4118 and 5131 of SEQ ID NO:1, wherein said transgenic knockout mouse is a model for selecting or screening psychoactive products, and wherein said transgenic knockout mouse exhibits disorders of social investigation and short-time memory disorders.

8. The transgenic mouse of claim 7, wherein said inactivated allele is obtained from a construct comprising a nucleic acid sequence derived from the same mouse or from a mouse that is different from the mouse into which said construct is inserted and wherein said construct is selected from the group consisting of: (i) constructs which do not comprise the region between nucleotide positions 4118 and 5131 of the genomic sequence SEQ ID NO:1 encoding a Stable Tubulin Only Polypeptide Protein (STOP) and (ii) constructs comprising 4.1 kb of the Stable Tubulin Only Polypeptide Protein (STOP) gene corresponding to the sequence consisting of nucleotides 1 to 4118 of SEQ ID NO:1, the gene encoding β-galactosidase, placed under the control of the endogenous Stable Tubulin Only Polypeptide Protein (STOP) promoter, a neomycin resistance gene under the control of the PGK promoter, 1.57 kb of sequence of the Stable Tubulin Only Polypeptide Protein (STOP) gene corresponding to the sequence consisting of nucleotides 5131 to 6701 of SEQ ID NO:1 and, finally, the thymidine kinase gene under the control of PGK promoter.

9. The transgenic knockout mouse of claim 8, wherein the constructs comprise a region of the Stable Tubulin Only Polypeptide Protein (STOP) promoter in combination with a reporter gene, said reporter gene being a green fluorescent protein gene.

* * * * *